US006124432A

United States Patent [19]

Kawai et al.

[11] Patent Number: 6,124,432

[45] Date of Patent: *Sep. 26, 2000

[54] PROCESS FOR PURIFYING DERMONECROTIC TOXIN PRODUCED BY BORDETELLA AND TOXOID

[75] Inventors: Toru Kawai; Toshihiro Ushijima; Kozo Takase; Hideo Fujikawa, all of Kumamoto, Japan

[73] Assignee: Juridical Foundation The Chemo-Sero-Therapeutic Research Institute, Kumamoto, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/750,166

[22] PCT Filed: Jun. 7, 1995

[86] PCT No.: PCT/JP95/01125

§ 371 Date: Dec. 2, 1996

§ 102(e) Date: Dec. 2, 1996

[87] PCT Pub. No.: WO95/34322

PCT Pub. Date: Dec. 21, 1995

[30] Foreign Application Priority Data

Jun. 10, 1994 [JP] Japan .................................... 6/152834

[51] Int. Cl.$^{7}$ ............................. C07K 1/00; C07K 14/00; C07K 16/00; A23J 1/00

[52] U.S. Cl. .......................... 530/350; 530/412; 530/414; 530/415; 530/417; 530/419; 530/421; 514/2

[58] Field of Search .................................... 530/412, 414, 530/350, 415, 417, 419, 421; 514/2

[56] References Cited

FOREIGN PATENT DOCUMENTS 175 841 4/1986 European Pat. Off. .

OTHER PUBLICATIONS

Confer (Veterinary Microbiology, (37) 1993 pp 353–368).

Kobisch et al (The Veterinary Record vol. 124 pp 57–61), 1989.

Iwamatsu et al., "Relationship Between Serotypes, Dermonecrotic Toxin Production of *Pasteurella Mulotcida* Isolates and Pneumonic Lesions of Porcine Lung", Jpn. J. Vet. Sci., vol. 50, No. 6, p. 1200–1206, 1988.

Elias et al., "Clinical and Pathological Effects of the Dermonecrotic Toxin of *Brodetella Bronchiseptica* and *Pasteurella Multocida* in Specific–Pathogen–Free Piglets", Jpn. J. Vet. Sci., vol. 52, No. 4, p. 677–688, 1990.

Endoh et al., "Purification and Characterization of Heat–Labile Toxin from *Bordetella Bronchiseptica*", Microbiol. Immunol., vol. 30, No. 7, p. 659–673, 1986.

Horiguchi et al., "Simplified Procedure for Purification of *Bordetella Bronchiseptica* Dermonecrotic Toxin", FEMS Microbiology Letters, vol. 66, p. 39–44, 1990.

Sekiya, "Effects of *Bordetella Pertusiss* Components on IgE and IgG1 Responses", Microbiol. Immunol., vol.27, No. 11, p. 905–915, 1983.

Horiguchi et al., "Purification and Characterization of *Bordetella Bronchiseptica* Dermonecrotic Toxin", Microbial Pathogenesis, vol. 6, p. 361–368, 1989.

Chanter et al., "Interactions Between *Bordetella Bronchiseptica* and Toxigenic *Pasteurella Multocida* in Atrophic Rhinitis of Pigs", Research in Veterinary Science, vol. 47, p. 48–53, 1989.

De Jong et al., "A Field Evaluation of Nobi–Vac Atrophic Rhinitis Vaccine", The Veterinary Quarterly, vol. 9, No. 1, p. 49–59, Jan., 1987.

Baalsrud, "Vaccination Against Atrophic Rhinitis: Effect on Clinical Symptoms, Growth Rate and Turbinate Atrophy", Acta Vet. Scand., vol. 28, p. 305–311, 1987.

Barfod et al., "Influence of Vaccination of Sows with Bordetella–Pasteurella Vaccines on the Occurrence of Atrophic Rhinitis Among Their Offspring After Experimental Infection with *Bordetella Bronchiseptica* and Toxigenic *Pasteurella Multocida*", Nord. Vet.–Med., vol. 36, p. 337–345, 1984.

Pedersen et al., "Effect on the Incidence of Atrophic Rhinitis of Vaccination of Sows with a Vaccine Containing *Pasteurella Multocida* Toxin", Nord. Vet–Med., vol. 34, p. 293–302, 1982.

Giles et al., "Vaccination of Pigs with *Bordetella Bronchiseptica*", Veterinary Bulletin, vol. 53, No. 4, p. 327–338, Apr., 1983.

Kamp et al., "Atypical Pasteurella Strains Producing a Toxin Similar to the Dermonecrotic Toxin of *Pasteurella Multocida* Subspecies *Multocida*", The Veterinary Record, p. 434–437, Apr. 28, 1990.

Rutter et al., "Cell Culture Assay for Toxigenic *Pasteurella Multocida* From Atrophic Rhinitis of Pigs", The Veterinary Record, p. 393–396, Apr. 21, 1984.

De Jong et al., "Investigation Into the Pathogenesis of Atrophic Rhinitis in Pigs", The Veterinary Quarterly, vol. 8, No. 3, p. 204–214, Jul., 1986.

Foged et al., "Protection Against Progressive Atrophic Rhinitis by Vaccination with *Pasteurella Multocida*–toxin Purified by Monoclonal Antibodies", The Veterinary Record, vol. 125, p. 7–11, Jul. 1, 1989.

*Primary Examiner*—Mark Navarro

*Attorney, Agent, or Firm*—Browdy and Neimark

[57] ABSTRACT

The present invention aims at providing a method for preparing dermonecrotic toxin, an improved toxoid of dermonecrotic toxin produced by Bordetelia and a toxoid mixture comprising said improved toxoid of dermonecrotic toxin produced by Bordetella and a toxoid of dermonecrotic toxin produced by Pasteurella. There is provided a method for partially purifying dermonecrotic toxin which comprises bringing a dermonecrotic toxin-containing solution into contact with a chromatographic gel sulfated by direct sulfation or a chromatographic gel to which a sulfated molecule is covalently bonded to thereby make the dermonecrotic toxin adsorbed on the gel, and eluting the adsorbed dermonecrotic toxin from the gel. There is also provided a toxoid obtained from dermonecrotic toxin produced by Bordetella, said dermonecrotic toxin being prepared by the above method for partially purifying dermonecrotic toxin, and a toxoid mixture prepared by mixing said toxoid and a toxoid of dermonecrotic toxin produced by toxigenic Pasteurella, said toxoid mixture being safe and effective for preventing the atrophic rhinitis in pigs.

14 Claims, 7 Drawing Sheets

OTHER PUBLICATIONS

Ohgitani et al., "Characterization of Haemagglutinin from *Bordetella Bronchiseptica*", Vaccine, vol. 9, p. 653–658, Sep., 1991.

Ostle et al., "Reducing the Effects of Enzootic Pneumonia and Atrophic Rhinitis", Veterinary Medicine, p. 772–775, Aug., 1986.

Nakai et al., "Purification of Dermonecrotic Toxin from a Sonic Extract of *Pasteurella Multocida* SP–72 Serotype D", Infection and Immunity, vol. 46, No. 2, p. 429–434, Nov., 1984.

Zhang et al., "Purification and Characterization of the Heat–Labile Toxin of *Bordetella Pertussis*", Infection and Immunity, vol. 59, No. 10, p. 3754–3759, Oct., 1991.

Roop, II et al., "Virulence Factors of *Bordetella Bronchiseptica* Associated with the Production of Infectious Atrophic Rhinitis and Pneumonia in Experimentally Infected Neonatal Swine", Infection and Immunity, vol. 55, No. 1, p. 217–222, Jan. 1987.

Kume et al., "Properties of Dermonecrotic Toxin Prepared from Sonic Extracts of *Bordetella Bronchiseptica*", Infection and Immunity, vol. 52, No. 4, p. 370–377, May, 1986.

Montaraz et al., "Identification of a 68–Kilodalton Protective Protein Antigen from *Bordetella Bronchiseptica*", Infection and Immunity, vol. 47, No. 3, p. 744–751, Mar., 1985.

Namioka et al., "Serological Studies on *Pasteurella Multocida*. I. A Simplified Method for Capsule Typing of the Organism", Connell Vet., vol. 51, p. 498–507, 1961.

Jayappa et al., "Evaluation of Efficacy of *B. Bronchiseptica–E Rhusiopathiae–P. Multocida* Types A and D–Bacterin–Toxoid in Controlling Turbinate Atrophy Caused by Toxigenic *P. Multocida*", Proc. Int. Pig Vet. Soc. Congr., p. 44, 1988.

Cookson et al., "Tracheal Cytotoxin: A Conserved Virulence Determinant of all Bordetella Species", J. Cell Biochem, 11B (Suppl.), p. 124, 1987.

Goodnow et al., "Control of Atrophic Rhinitis with a *Bordetella Bronchiseptica* Bacterin", Veterinary Medicine/ Small Animal Clinician, vol. 72, p. 1210–1212, Jul. 1977.

Dugal et al., "Enhanced Adherence of *Pasteurella Multocida* to Porcine Tracheal Rings Preinfected with *Bordetella Bronchiseptica*", Can. J. Vet. Res., vol. 56, p. 260–264, 1992.

"The 111th Japan Vet. Soc. Lecture Abst.", p. 183, 1991.

Cellulose sulfate ester gel column chromatography

High performance liquid chromatography on TSK gel G3000SW

Lanes 1 and 2: Molecular weight marker; Lane 3: Extract of bacterial cell homogenate; Lane 4: Cellulose sulfate ester gel; Lane 5: SP TOYOPEARL; Lane 6: TSK gel G3000SW Fig. 7A
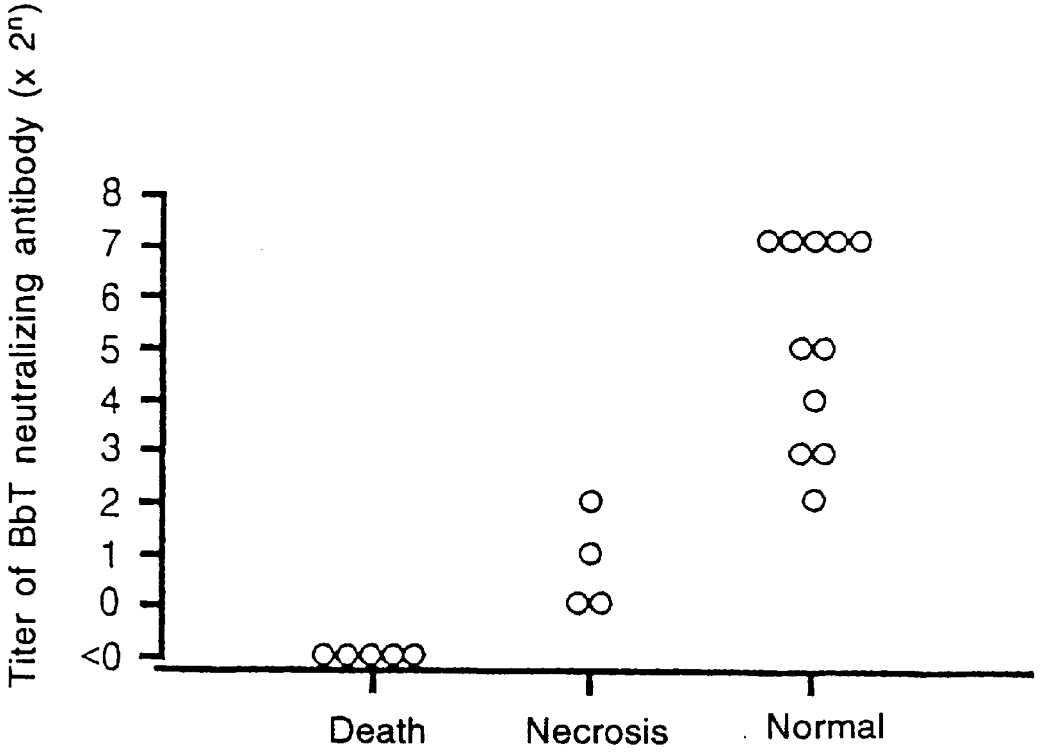
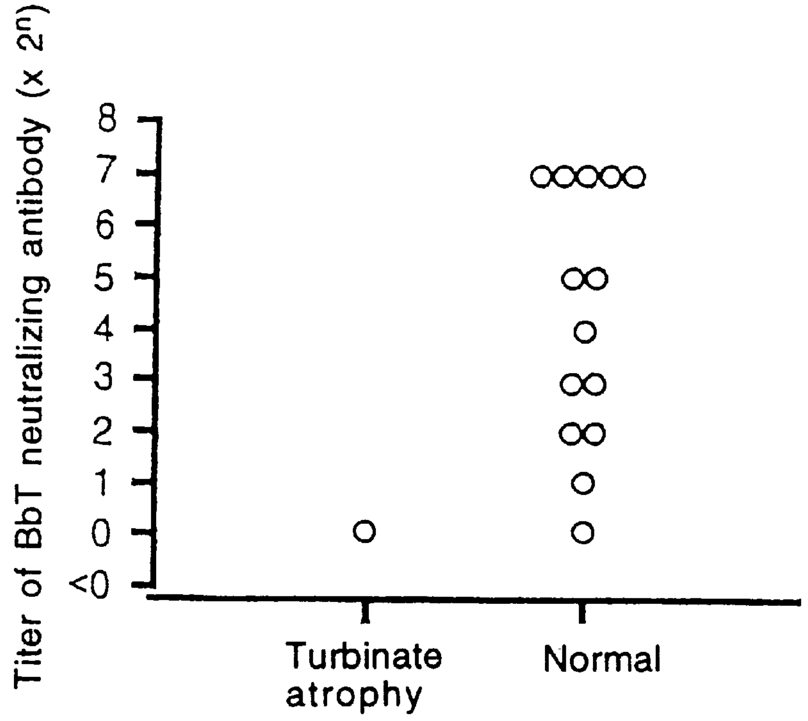
Fig. 7B

PROCESS FOR PURIFYING DERMONECROTIC TOXIN PRODUCED BY BORDETELLA AND TOXOID

TECHNICAL FIELD OF THE INVENTION

The present invention relates to a medicament for prophylaxis of swine infectious diseases. More particularly, the present invention relates to an improved toxoid of dermonecrotic toxin produced by Bordetella, a toxoid mixture comprising said toxoid and a toxoid of dermonecrotic toxin produced by Pasteurella and a process for preparing said toxoid.

BACKGROUND OF THE INVENTION

Atrophic rhinitis (hereinafter also referred to as "AR") is a swine chronic respiratory disease which has extremely potent infectivity with primary symptoms being turbinate atrophy, hypoplasia, epistaxis, twisting of the snout and induction of other respiratory diseases, and the like. This disease is known to be caused by a toxigenic *Bordetella bronchiseptica* (hereinafter also referred to as "Bb") and a toxigenic *Pasteurella multocida* (hereinafter also referred to as "Pm") which infect at the mucosa of an upper respiratory tract. Bb possesses hemagglutinin and pili as an adherence factor and thus easily attaches to the nasal mucosa while Pm does not have such an adherence factor and hence hardly colonizes by itself. Accordingly, for the establishment of Pm infection, a predisposing factor causing a lesion at the nasal mucosa is necessary, said factor being typically Bb. Pathological factors involved in the cause of lesion in the nasal mucosa are known to be a tracheal cytotoxin and a dermonecrotic toxin. In an experimental infection, a pig is infected with Bb, and several days later, followed by intranasal infection with Pm, to cause a severe AR as observed in a field farm.

Bordetella includes *B. pertussis, B. parapertussis, B. bronchiseptica, B. avium,* and the like, which produce a variety of biologically active substances. Bb dermonecrotic toxin (hereinafter also referred to as "BbT") is one of such substances and is produced by any Bordetella. BbT having biological activities such as a hemorrhagic necrotic activity, an activity to cause turbinate atrophy, an activity to cause hypoplasia, a lethal activity, a vasoconstrictive activity in the smooth muscle, an activity to cause interruption in a local blood circulation, an activity to cause splenoatrophy, an activity to inhibit an antibody production, and the like was found to play an important role in Bordetellosis. Furthermore, it was found that BbT also plays an important role in the formation of pneumonic focus in piglets (Roop II, R. M. et al., Infect. Immun., 55, p.217–222 (1987)).

On the other hand, a part of *Pasteurella multocida* or a part of atypical Pasteurella produce Pm dermonecrotic toxin (hereinafter also referred to as "PmT"). PmT having biological activities such as a hemorrhagic necrotic activity, an activity to cause turbinate atrophy, an activity to cause hypoplasia, a lethal activity, an activity to cause interruption in a local blood circulation, an activity to cause splenoatrophy, and the like has been found to play an important role in the onset of disease by the toxigenic Pm. Furthermore, it was found that PmT is closely related to the formation of pneumonic focus in pigs by the toxigenic Pm (Iwatsu, S. and Sawada, T.; Jpn. J. Vet. Sci., 50, p.1200–1206 (1988)). Although both BbT and PmT are not secreted into a culture medium but accumulate within bacterial cells, they are released out of the bacterial cells into a culture supernatant due to bacteriolysis after a long term culture. In the in vivo process, dermonecrotic toxin released out of the bacterial cells due to bacteriolysis affect the living body.

Under the above-mentioned circumstances, the role of dermonecrotic toxin in protection in the living body still remains unclear, and for elucidating the mechanism of the protection, there is a need to develop a process for a large scale preparation of dermonecrotic toxin and to develop a toxoid of dermonecrotic toxin for use in prophylaxis of the disease. However, it has been difficult to purify dermonecrotic toxin due to its properties, i.e. unstability to heat, self-agglutination easily caused as purification processes proceed, formation of a complex with bacterial cell-derived substances such as lipids, acid proteins, hydrophobic substances, etc. Furthermore, since BbT and PmT do not immunologically cross-react to each other in spite of their similarity in biological activities, it has been earnestly desired to develop a BbT-PmT toxoid mixture which is safe and effective from the viewpoint of veterinary and pig breeding industry.

A hitherto known process for partially purifying dermonecrotic toxin from a bacterial dermonecrotic toxin-containing solution, especially from a Bordetella bacterial cell extract, includes a process using a ion exchange chromatography (Kume, K. et al., Infect. Immun., 52(4), p.370–377 (1986)). However, this process disadvantageously shows poor reproducibility. A process for partially purifying dermonecrotic toxin is also known which utilizes dialysis, a sucrose-gradient ultracentrifugation and a gel filtration chromatography (Endoh, M. et al., Microbiol. Immunol., 30, (7), p.659–673 (1986)). However, this process also shows disadvantageously poor reproducibility, and in addition, does not provide a sufficient degree of purification in spite of many steps.

Another example includes a process utilizing treatment with a nucleic acid-removing agent, an anion exchange chromatography and a hydroxyapatite adsorption chromatography (Horiguchi, Y. et al., Microbiol. Pathogen., 6, p.361–368 (1989)). However, this process is also disadvantageous in that it requires a costly reagent, a nucleic acid-removing agent, and involves many steps. There is also a process utilizing a nucleic acid-removing agent, a dialysis and a cation exchange chromatography (Horiguchi, Y. et al., FEMS Microbiol. Letters, 66, p.39–44 (1990)). Although this process shows high reproducibility and can provide dermonecrotic toxin with comparatively high purity, it also disadvantageously requires a costly reagent as in the above process.

Still another example is a process using a salting-out and a dye ligand affinity chromatography (Zhang Y. L. and Sekura R. D., Infect. Immun., 59(10), p.3754–3759 (1991)). Although this process shows a high reproducibility, it disadvantageously provides an insufficient degree of purification.

Inactivated AR vaccines reported so far includes three types, i.e. an inactivated Bb plain vaccine, an inactivated Pm plain vaccine and a Bb/Pm combined inactivated vaccine, each having been studied or put into practical use.

A Bb inactivated vaccine includes one comprising killed bacteria inactivated with formalin, glutaraldehyde, etc. supplemented with aluminum gel or an oil adjuvant (Goodnow, R. A., Vet. Med. Small Anim. Clin., 72, p.1210–1212 (1977); Nakase, Y. et al., Proc. Int. Pig Vet. Soc. Congr., 8, (1976); Giles, C. J. and Smith, I. M., Vet. Bull.(London), 53, p.327–338 (1983)). It was also found that a 68 kDa protein, which is present on the outer membrane of Bb and has an adenylate cyclase activity, exhibits a prophylactic activity against atrophic rhinitis (Montaraz J. A. et al., Infect. Immun., 47,, p.744–755 (1985)). A component vaccine comprising a Bb-produced fibrous hemagglutinin as a primary component is also known (Hansen, G. R. et al.; In Atrophic rhinitis in pigs (Ed. Peterson, K. B. and Nielsen, N. C.) Communication of the European Communities, Luxembourg, p.89–97 (1983), and Ohgitani, T. et al., Vaccine, 9, p.653–658 (1991)). There is also reported that a vaccine supplemented with dermonecrotic toxin for providing an antitoxin is not efficacious (Soderlind, O. and Bergstrom, G., Proc. Int. Pig Vet. Sci. Congr., p.175 (1984); Marel, C. M. von der. et al., Proc. Int. Pig Vet. Sci. Congr., p.170 (1984)).

On the other hand, an inactivated Pm plain vaccine includes Pm toxoid (Pedersen, K. B. and Barfod, K., Nord. Vet. Med., 31, p.293–302 (1982); Foged, N. T. et al., Vet. Rec., 125, p.7–11 (1989)), which has been studied or put into practical use.

A Bb/Pm combined inactivated vaccine includes (1) a mixture of killed Bb with killed PmT-producing PmD type bacteria, the mixture which is further supplemented with PmT non-producing bacteria, or a mixture of Bb and PmT toxoid (Barfod, K. and Pedersen, K. B., Nord. Vet. Med., 36, p.337–345 (1984); Baalsrud, K. J., Acta Vet. Scand., 28, p.305–311 (1987)); de Jong, M. F. et al., Vet. Quart., 9, p.49–59 (1987); Kobisch, M. and Pennings, A., Vet. Rec., 124, p.57–61 (1989)), for the purpose of prophylaxis of AR alone; (2) a mixture of killed Bb with killed PmD type PmT-producing bacteria and killed PmA type bacteria (Ostle, A. G. et al., Vet. Med., p.772–775 (1986)), for the purpose of prophylaxis of AR and pneumonia; and (3) a mixture of killed Bb with killed PmA type bacteria, killed *Erysipelothrix insidiosa* and PmT toxoid (Jayappa, H. et al., Int. Pig Vet. Soc. Congr., p.44 (1988)), for the purpose of prophylaxis of other diseases as well as AR and pneumonia, any of (1) to (3) having been put into practical use.

Since BbT plays an important role in the turbinate atrophy and the pneumonic focus formation by Bb infection, Zoop II, R.M. et al. has pointed out a need of BbT toxoid (Infect. Immun., 55, p.217–222 (1987)). However, they never refer to a combination of BbT and PmT toxoids. Chanter, N. et al. has proposed that a combination of PmT toxoid with the important toxin of Bb is more effective since the lesion in the swine nasal mucosa induced by cooperative activity of BbT and PmT provides environments favorable to Bb and Pm propagation (Res. Vet. Sci., 47, p. 48–53 (1989)).

However, a production of a BbT neutralizing antibody has not yet been successfully enhanced with a vaccine comprising a fraction having a BbT activity (Soderlind, O. and Bergstrom, G., Proc. Int. Pig Vet. Sci. Congr., p. 175 (1984); Marel, C. M. von der. et al., Proc. Int. Pig Vet. Sci. Congr., p.170 (1984)). On the other hand, Nakai et al. revealed that a production of a neutralizing antibody is enhanced in pigs and mice with a highly purified BbT toxoid (The 111th Japan Veterinary Society, lecture abstract, p.183 (1991)). However, they also never refer to a combination of said BbT toxoid and PmT toxoid.

DISCLOSURE OF THE INVENTION

The present inventors have earnestly studied in order to find out a method for efficiently purifying dermonecrotic toxin, and as a result, have found (1) that a partially purified dermonecrotic toxin with a lowered content of endotoxin can be easily obtained at a comparatively high rate of recovery by conducting a chromatography on a dermonecrotic toxin-containing solution, e.g. a Bordetella bacterial extract, using either a chromatographic gel sulfated by direct sulfation or a chromatographic gel to which a sulfated molecule is covalently bonded, such as a cellulose sulfate ester gel, a heparin-immobilized adsorption gel or a sulfated alkyl-immobilized adsorption gel, (2) that a highly purified dermonecrotic toxin can be easily obtained at a comparatively high rate of recovery by further conducting a dialysis, a cation exchange chromatography and a gel filtration chromatography on the above dermonecrotic toxin partially purified by using either a chromatographic gel sulfated by direct sulfation or a chromatographic gel to which a sulfated molecule is covalently bonded, and (3) that an immune response is extremely improved in the dermonecrotic toxin partially purified by using either a chromatographic gel sulfated by direct sulfation or a chromatographic gel to which a sulfated molecule is covalently bonded, as compared to the dermonecrotic toxin in the unpurified Bordetella bacterial cell extract.

Furthermore, the present inventors have confirmed that a toxicity-reduced product of a fraction of dermonecrotic toxin with a chemical treatment can effectively and safely be used for prophylaxis of atrophic rhinitis in pigs, said fraction of dermonecrotic toxin being prepared by bringing said Bordetella bacterial cell extract into contact with either a chromatographic gel sulfated by direct sulfation or a chromatographic gel to which a sulfated molecule is covalently bonded to thereby make the dermonecrotic toxin adsorbed on the gel and separated from contaminants, followed by elution of the dermonecrotic toxin from the gel. Thus, the present invention has been completed.

In order that Pm infection is established in pigs, preinfection of Bb as a factor for causing the lesion at the nasal mucosa in pigs is necessary. Where pigs are immunized with BbT antitoxin, there can be reduced a colonization of Pm on the nasal mucosa and the turbinate atrophy by Bb and Pm infection. However, since there can be seen notable variability in effects from individual to individual, it was revealed that BbT toxoid alone is not sufficient for an AR inactivated vaccine.

Based on the above-mentioned findings, the present inventors have earnestly studied in order to develop a toxoid mixture, and as a result, have found that a toxoid mixture prepared by mixing a toxoid obtained from toxin purified up to a specific activity of 37,000 MND/mg protein or more from a Bordetella bacterial cell extract by using a cellulose sulfate ester gel etc. with a toxoid obtained from PmT produced by toxigenic Pm can effectively and safely be used for prophylaxis of atrophic rhinitis in pigs. Thus, a toxoid mixture, the second embodiment of the present invention, is provided.

A minimum necrotic dose (MND) as used herein is such that 1 MND is defined as a minimum amount of dermonecrotic toxin which produces a necrotic spot of not less than 5 mm diameter one day after intracutaneous injection to guinea pig in the presence of 1 $\mu$g/ml of a lipopolysaccharide (e.g. one derived from *E. coli,* serotype 0111:B4).

BRIEF DESCRIPTION OF THE DRAWINGS

FIGS. 7A and 7B show results of study on protection line of a BbT neutralizing antibody.

BEST MODE FOR CARRYING OUT THE INVENTION

Figure 1:
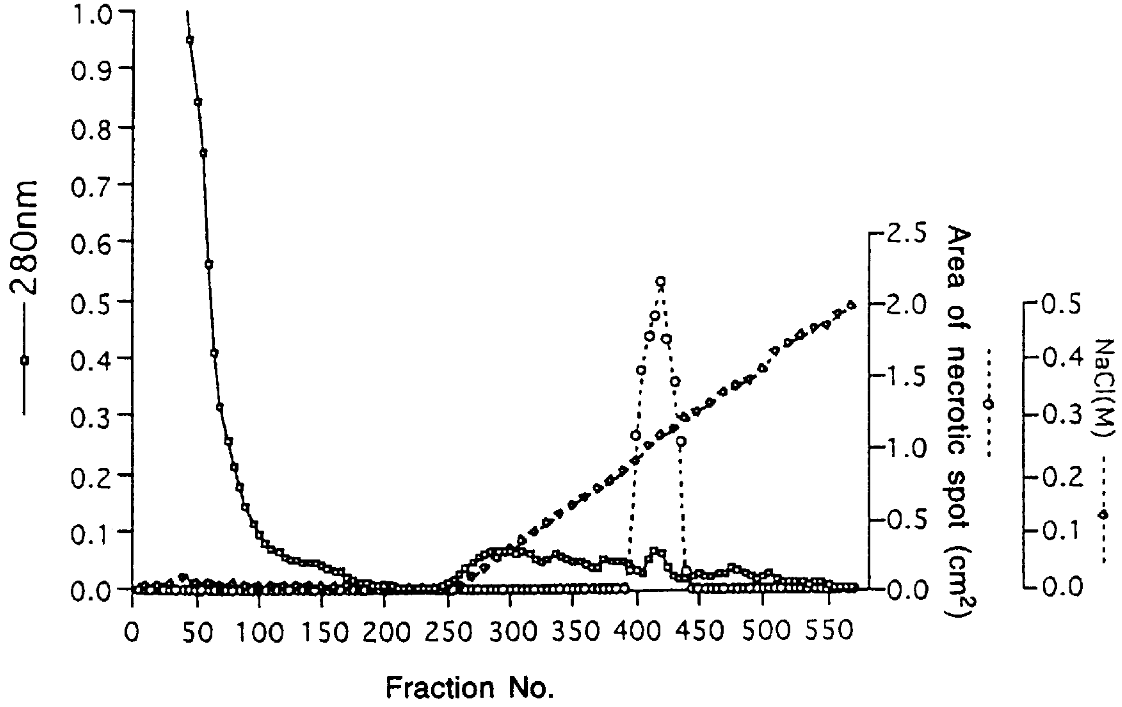
FIG. 1 shows a chromatogram in one step of a method for purifying dermonecrotic toxin according to the present invention.

The present invention provides a method for partially purifying dermonecrotic toxin which comprises bringing a dermonecrotic toxin-containing solution into contact with either a chromatographic gel sulfated by direct sulfation or a chromatographic gel to which a sulfated molecule is covalently bonded to thereby make the dermonecrotic toxin adsorbed on the gel, followed by the elution thereof from the gel. The present invention also provides a BbT toxoid derived from BbT obtained by said method for partially purifying dermonecrotic toxin, and a toxoid mixture which is prepared by mixing said BbT toxoid with a toxoid derived from PmT produced by toxigenic Pm, said toxoid mixture being safe and effective for prophylaxis of atrophic rhinitis in pigs.

A dermonecrotic toxin-containing solution as used herein as a starting material includes a bacterial cell extract from Bb, *B. pertussis* and *B. parapertussis.* The starting material of the present invention also includes an extract from cells wherein BbT is expressed by means of a genetic engineering technique. A preferred extract used herein is a bacterial cell extract from Bb. Bb is cultured in a usual manner by an agar culture on Bordet-Gengou medium, Macconkey medium, and the like, or by a standing culture, a shaking culture or an aeration spinner culture in a liquid medium such as a peptone medium (Horiguchi, Y. et al., Microb. Pathogen., 6, p.361–368 (1989)), Cohen-Willer medium, Stenner-Scholte medium, and the like. Bacterial culture on agar medium are suspended in a starting buffer of a cellulose sulfate ester gel using a Conradi stick etc. Bacterial culture in liquid medium are, after recovering bacterial cells by centrifugation, suspended in a starting buffer of a cellulose sulfate ester gel.

The obtained suspension of bacterial cells can be purified by the method of Kume, K. et al. (Infect. Immun. 52(4), p.370–377 (1986)), by the method of Endoh, M. et al. (Microbial. Immunol., 30(7), p.659–673 (1986)), by the method of Horiguchi, Y. et al. (Microbial. Pathogen., 6, p.361–368 (1988) or FEMS Microbiol. Letters, 66, p.39–44 (1990)), by the method of Zhang Y. L. and Sekura R. D. (Infect. Immun., 59(10), p.3754–3759 (1991)), or by an adsorption chromatography using either a chromatographic gel sulfated by direct sulfation such as a cellulose sulfate ester gel or a chromatographic gel to which a sulfated molecule is covalently bonded. In accordance with the present invention, however, the most preferable embodiment is that the suspension is purified by an adsorption chromatography using either a chromatographic gel sulfated by direct sulfation or a chromatographic gel to which a sulfated molecule is covalently bonded.

The suspension of bacterial cells is subjected to a sonication, an enzyme treatment, a pressing, a repetition of freezing-thawing, etc. to homogenize the cells, and cellular debris are removed by centrifugation or membrane filtration. Thus obtained bacterial extract is directly, or after further pretreatment for purification via the use of a nucleic acid-removing agent, a salting-out, ultracentrifugation, etc., subjected to a method of the present invention. In accordance with the method of the present invention, the pretreatment is not always necessary but instead a bacterial cell extract can directly be subjected to an adsorption chromatography using either an adsorption gel having a sulfated molecule as a ligand or an adsorption gel sulfated by direct sulfation, thereby to make the procedure quite simple and convenient.

As used herein, a chromatographic gel sulfated by direct sulfation or a chromatographic gel to which a sulfated molecule is covalently bonded are exemplified as follows:

"A chromatographic gel sulfated by direct sulfation" as used herein means a chromatographic gel (e.g. cellulose) wherein the gel itself is directly sulfated by reaction with a sulfating agent such as chlorosulfonic acid, sulfuric anhydride in the presence of an organic solvent such as pyridine via, for example, an ester bond, including typically a cellulose sulfate ester gel wherein a sulfate ester is introduced into a globular cellulose composed of a crystalline cellulose or a crystalline region and non-crystalline region cellulose. The obtained cellulose sulfate ester retains a shape of a starting material, is insoluble in an aqueous solvent, is excellent in a physical stability, and hence is suitable for use as a chromatographic gel. These starting celluloses are already commercially available, for example, as Avicel (manufactured by Asahi Kasei Kogyo K. K.), Cellulofine GC-15, GH-25, GC-100, GC-200 (manufactured by Chisso Corporation), and the like. The starting cellulose can be sulfated by the above-mentioned methods or some sulfated cellulose are commercially available as, for example, "Sulfated Cellulofine" (manufactured by Chisso Corporation).

"A chromatographic gel to which a sulfated molecule is covalently bonded" as used herein means a chromatographic gel comprised of a natural high molecular weight polymer such as a cross-linked cellulose, a cross-linked dextran or a cross-linked agarose gel or a synthetic high molecular weight polymer such as a hydrophilic vinyl polymer or styrene divinylbenzene copolymer, to which heparin, a highly sulfated glucosaminoglycan, or sulfopropyl group, a kind of a sulfated alkyl, or a blue dye having or sulfone group is covalently bonded by CNBr procedure, etc., including many commercially available products. A chromatographic gel to which heparin is bonded includes "Heparin Sepharose CL-6B" (Pharmacia), "Affigel Heparin Gel" (Bio-Rad), "Heparin Cellulofine" (Seikagaku Kogyo K. K.), and the like. A chromatographic gel to which a blue dye is bonded includes "Affigel Blue Gel" (Bio-Rad), "AF-blue Toyopearl" (Toso K. K.), "Blue Cellulofine" (Seikagaku Kogyo K. K.), and the like. A chromatographic gel to which sulfopropyl group is bonded includes "SP-Sephadex" (Pharmacia), "SP-Toyopearl 650M" (Toso K. K.), and the like.

Purification and collection of dermonecrotic toxin from a dermonecrotic toxin-containing solution, especially a Bordetella bacterial cell extract, using an adsorption gel having a sulfate group as a ligand or an adsorption gel sulfated by direct sulfation, is carried out in the following manner. Although the present invention is illustrated by the use of a cellulose sulfate ester gel as a preferable embodiment, any other gel can also be used under similar conditions.

A cellulose sulfate ester gel is previously equilibrated with a buffer having around neutral pH (pH 7 to 9) and an appropriate specific electric conductivity, i.e. that being standardized for washing and elution in a gel chromatography (usually 20 mS/cm or less, generally 3 to 20 mS/cm, more generally 5 to 20 mS/cm although it may vary to some extent depending on a kind of a gel) or less, for example, 0.02 M phosphate buffer supplemented with 0 to 0.2 M sodium chloride, and then subjected to an adsorption procedure for dermonecrotic toxin. A series of purification procedures such as an adsorption of dermonecrotic toxin to a cellulose sulfate ester gel, washing of the gel, elution of dermonecrotic toxin, etc. can be conducted in an industrially usual manner such as a batch process or a column process. Where a batch process is employed, a cellulose sulfate ester is placed in a Bordetella bacterial cell extract and the mixture is slowly stirred at a temperature of 0 to 30° C. at a pH range of around 7.0 to 9.0 for about 10 to 60 minutes to thereby make dermonecrotic toxin adsorbed onto the cellulose sulfate ester. In this case, a cellulose sulfate ester is suitably concentrated or diluted prior to adsorption procedure so that a specific electric conductivity of the Bordetella bacterial cell extract falls within the above-mentioned range, generally 3 to 20 mS/cm, or less.

After adsorption is completed, a mixture of the extract and the gel is loaded on a filter and filtration with suction is conducted to separate the gel from the filtrate. To the separated gel is poured a suitable buffer having the above fixed range of a specific electric conductivity (generally around 3 to 20 mS/cm) or less and pH of around 5 to 10, for example, 0.02 M phosphate buffer supplemented with 0.1 M sodium chloride, to wash the gel with suction. To the gel is then poured a suitable buffer having pH of around 5 to 10 and a specific electric conductivity of more than the above fixed range and generally of less than 130 mS/cm (a preferable range is, for example, around 22 to 46 mS/cm), for example, a phosphate buffer supplemented with 0.2 M to 0.5 M sodium chloride, to elute the adsorbed dermonecrotic toxin.

Where a column process is employed, conditions of a starting material, a buffer for washing and a buffer for elution may be similar to those in a batch process. It is recommended that a rate of passage of the buffers is adjusted to around 10 $ml/cm^2/hr$ to 500 $ml/cm^2/hr$.

The method for purification according to the present invention enables specific adsorption of dermonecrotic toxin in a dermonecrotic toxin-containing solution, provides as high as several ten fold to 110-fold purification degree of dermonecrotic toxin, and shows a good recovery of dermonecrotic toxin, 40% to 100%. Endotoxin, which is responsible for side effects such as fever or shock and is contained in a large amount in an extract of bacterial cell homogenate together with dermonecrotic toxin, is not adsorbed onto the cellulose sulfate ester gel and thereby reduced to 1/30 to 1/800. The obtained purified dermonecrotic toxin shows as high as $4\times10^5$ to $3\times10^6$ MND/mg protein of a specific activity and forms a main band in an SDS-polyacrylamide gel electrophoresis.

As mentioned above, according to the method of the present invention, a desired dermonecrotic toxin can be obtained from a starting dermonecrotic toxin-containing solution at a good yield and purity, the procedures are quite simple, and the chromatographic adsorbent used for purification can be prepared or is available at a low cost, said adsorbent being extremely excellent from economical point of view without no deterioration after being used repeatedly. Accordingly, the method of the present invention is a quite excellent method for industrial production of dermonecrotic toxin. In addition, the method of the present invention can also be used in combination with the conventional cation exchange chromatography, gel filtration chromatography, etc. to further increase the purity to thereby provide more excellent results than those obtained by the conventional methods.

Dermonecrotic toxin purified by the method of the present invention is transformed into a toxoid which is deprived of a toxin activity while retaining immunogenicity by treatment with a chemical reagent. Transformation of dermonecrotic toxin into a toxoid can be conducted in a usual manner, for example, by using formalin (Nakai, T. et al., Infec. Immun., 46, p.429–434 (1984)) or by using glutaraldehyde (Endoh, M. et al., Microbiol. Immunol., 30, p.659–673 (1986)), etc. In order to induce humoral immunity by administering said toxoid into the living body, an adjuvant is administered together. An exemplary adjuvant to be used includes aluminum gel, oil adjuvant, saponin, etc. Said toxoid shows a higher immunogenicity than that of an unpurified fraction of dermonecrotic toxin and is also safe enough, which are confirmed by the data in Examples as described blow.

The partially purified dermonecrotic toxin obtained by the method of the present invention has a high purity and is deprived of most of endotoxin, and hence, is useful for preparing a vaccine for animal. In addition, where the purity of the partially purified dermonecrotic toxin is further increased by employing the method of the present invention in combination with the conventional purification procedures, it can also be used for preparing various reagents or medicaments or even for preparing *Bordetella pertussis* vaccine for human.

In most cases of natural infection of Bb, a BbT neutralizing antibody does not appear but a bacteria-agglutinating antibody increases at a high rate, which has been used for serological diagnosis of this disease. According to the present inventor's survey, only two pigs (0.6%) in one farm (2.1%) were detected positive for a BbT neutralizing antibody among 327 pigs in 48 farms in 15 prefectures where AR occurred. The conventional Bb killed vaccines increase a bacteria-agglutinating antibody to interfere the diagnosis. However, when a purity of BbT is further increased by combining the method for purification of the present invention with the conventional purification procedures, a toxoid can be prepared which provides a neutralizing antibody but does not increase a bacteria-agglutinating antibody. A vaccine or toxoid which enables serological distinction between a vaccine-induced antibody and an infection-induced antibody is called a "marker vaccine". For example, in specific pathogen free (SPF) farms, if by any chance Bb infection occurred while the toxoid of the present invention is used for prevention of AR, infected pigs can be detected by measuring a bacteria-agglutinating antibody.

Another aspect of the present invention provides a toxoid mixture comprising BbT toxoid prepared in accordance with the method for purification of the present invention and a toxoid of dermonecrotic toxin produced by Pasteurella.

For PmT as used herein, a starting Pm bacterial cell extract includes a bacterial cell extract from toxigenic Pm or atypical Pasteurella (Kamp, E. M. I. E. et al., Vet. Rec., 126, p.434–437 (1990)). Alternatively, a starting material of the present invention also includes an extract of cells where PmT is expressed by a genetic engineering technique. A preferred extract used herein is a bacterial cell extract from toxigenic Pm, which is cultured in a usual manner by a standing culture, a shaking culture or an aeration spinner culture in a liquid medium such as Heart infusion medium, trypticase soy broth, Luria-Bertani medium, meat infusion medium (de Jong, M. F. and Akkermans, J. P. W. M., Vet. Quart., 8, p.294–214 (1986)) or by an agar culture such as dextrose-starch medium, blood agar medium, YPC medium (Namioka, S. and Murata, M., Cornell Vet., 51, p.498–507 (1961)), and the like. Bacterial culture on an agar medium is suspended in a Tris buffer etc. using a Conradi stick etc.

Bacterial culture in a liquid medium is, after recovering bacterial cells by centrifugation, suspended in a suitable buffer for the next purification step. The suspension of bacterial cells is subjected to a sonication, an enzyme treatment, a pressing, a repetition of freezing-thawing, etc. to homogenize the cells, and cellular debris are removed by centrifugation or membrane filtration.

The cell extract is purified by an ion exchange chromatography, an affinity chromatography prepared with an antibody recognizing PmT, and the like. Alternatively, a supernatant obtained after culture of toxigenic Pm in a liquid medium for 24 to 65 hours can be used as a starting material for purification or directly subjected to a process of reducing toxicity.

The toxin fraction thus prepared is subjected to a process of detoxication by treatment with formalin, glutaraldehyde, etc. After completion of the detoxication, the buffer is replaced with a phosphate-buffered saline by dialysis etc. and thereto is added an adjuvant. An exemplary of an adjuvant which may be used includes aluminum gel, oil adjuvant, saponin, and the like. A toxoid mixture can be prepared by mixing a solution of one antigen at a concentration of twice as that of plain vaccine supplemented with an adjuvant with an equivalent amount of solution of another antigen at a concentration of twice as that of plain vaccine supplemented with an adjuvant.

The toxoid mixture obtained in accordance with the present invention not only is safe enough but also elicits both antibodies neutralizing BbT and PmT to thereby enable protection of pigs from the turbinate atrophy or hypoplasia due to both toxins.

The BbT toxoid and the toxoid mixture obtained in accordance with the present invention, when intramuscularly injected to a pregnant sow twice at an interval of 2 to 6 weeks at least one week prior to farrowing, protects their progeny from infection via a maternal antibody provided through colostrum. For the subsequent delivery, only one inoculation of the toxoid of the present invention prior to farrowing is sufficient for establishment of immunity. For the case of farms of sever AR infection, the toxoid of the present invention can also effectively be intramuscularly injected to piglets of not less than 7 days old twice at an interval of 2 to 6 weeks to thereby enable direct protection.

The present invention is illustrated in more detail by means of the following Preparations and Examples, but should not be construed to be limited thereto.

EXAMPLE

Preparation 1

Chlorosulfonic acid (117 g) is added dropwise to pyridine (600 ml) at a temperature not more than 0° C. and the mixture is stirred. After dropwise addition, the mixture is heated up to 65 to 70° C. Thereto is added Cellulofine GC-15 (80 g; manufactured by Chisso Corporation) and the mixture is stirred for reaction at 65 to 70° C. for 3 hours. After completion of the reaction, the mixture is cooled and 10% aqueous solution of sodium hydroxide is added to gradually neutralize the mixture. The gel is filtered off and washed sufficiently with 0.01 M phosphate-buffered saline to yield a cellulose sulfate ester gel.

Preparation 2

Chlorosulfonic acid (117 g) is added dropwise to pyridine (600 ml) at a temperature not more than 0° C. and the mixture is stirred. After dropwise addition, the mixture is heated up to 65 to 70° C. Thereto is added Avicel for chromatography (80 g; microcrystalline cellulose; manufactured by Asahi Kasei Kogyo K. K.) and the mixture is retained at 65 to 70° C. for 4 hours while stirring. After completion of the reaction, the mixture is cooled and 10% aqueous solution of sodium hydroxide is added to neutralize the mixture. The gel is filtered off and washed sufficiently with 0.01 M phosphate-buffered saline to yield a crystalline cellulose sulfate ester gel.

Preparation 3

Chlorosulfonic acid (82 g) is added dropwise to pyridine (500 ml) at a temperature of 0 to 5° C. and the mixture is stirred. After dropwise addition, the mixture is heated up to 65 to 70° C. Thereto is added Cellulofine GC-25 (80 g; manufactured by Chisso Corporation) and the mixture is stirred for reaction at 65 to 70° C. for 4 hours. After completion of the reaction, the mixture is cooled and 10% aqueous solution of sodium hydroxide is gradually added to neutralize the mixture. The gel is filtered off and washed sufficiently with 0.01 M phosphate-buffered saline (pH 7.2) to yield a cellulose sulfate ester gel.

Example 1

(Gradient elution from column)

A column (50 mm (i.d.) ×200 mm) was packed with a sulfate ester of Cellulofine GC-15 prepared as in Preparation 1 and equilibrated with 0.02 M phosphate buffer (pH 8.0; specific electric conductivity, around 3 ms/cm). A cell extract (200 ml) of Bb strain S611 was applied to the column. And then, the column was washed with the above buffer to wash out debris. Then, a gradient elution was carried out with a phosphate buffer (pH 8.0; specific electric conductivity, around 3 to 46 ms/cm) supplemented with 0 to 0.5 M sodium chloride to give a fraction containing dermonecrotic toxin with 9.1 mg of a total protein. A rate of recovery of dermonecrotic toxin was 39.6% and a purification degree (specific activity of purified dermonecrotic toxin fraction/specific activity of an extract of bacterial cell homogenate) was as high as 32.1.

Example 2

(Step-wise elution from column)

A column (252 mm (i.d.)×210 mm) was packed with a sulfate ester of Cellulofine GC-15 prepared as in Preparation 1 and equilibrated with 0.02 M phosphate buffer (pH 8.0; specific electric conductivity, around 3 ms/cm). A cell extract of Bb strain S611 (29 to 35 g of a total protein) was applied to the column. And then, the column was washed with 0.02 M phosphate buffer (pH 7.8 to 8.0; specific electric conductivity, around 3 to 17 ms/cm) supplemented with 0 to 0.15 M sodium chloride to wash out debris. Then, the dermonecrotic toxin was eluted with a phosphate buffer (pH 7.5 to 7.7; specific electric conductivity, around 30 to 46 ms/cm) supplemented with 0.3 to 0.5 M sodium chloride to give a fraction containing dermonecrotic toxin with 0.2 to 1.1 g of a total protein. As shown in Table 1, a rate of recovery of dermonecrotic toxin was 76 to 100% and a purification degree (specific activity of purified dermonecrotic toxin fraction/specific activity of an extract of bacterial cell homogenate) was as high as 22 to 114 with endotoxin being reduced to 0.1 to 3%.

TABLE 1

| Batch No. | Process | Total BbT activity (MND) | (Rate of recovery) | Total protein (a) (g) | (Rate of recovery) | Total endotoxin (b) (mg) | (Rate of recovery) | Specific activity (MND/mg protein) | Purification degree |
|---|---|---|---|---|---|---|---|---|---|
| 1 | Extract of bacterial cell homogenate | $5.55 \times 10^8$ | (100) | 34.3 | (100) | 59.6 | (100) | $1.62 \times 10^4$ | 1.0 |
| | Fraction of chromatographic purification | $4.20 \times 10^8$ | (75.7) | 1.12 | (3.3) | 1.80 | (3.02) | $3.75 \times 10^5$ | 23.2 |
| 2 | Extract of bacterial cell homogenate | $1.01 \times 10^9$ | (100) | 34.1 | (100) | 58.1 | (100) | $2.95 \times 10^4$ | 1.0 |
| | Fraction of chromatographic purification | $1.14 \times 10^9$ | (113.2) | 0.54 | (1.6) | 1.02 | (1.76) | $2.11 \times 10^6$ | 71.5 |
| 3 | Extract of bacterial cell homogenate | $4.30 \times 10^8$ | (100) | 35.3 | (100) | 86.7 | (100) | $1.22 \times 10^4$ | 1.0 |
| | Fraction of chromatographic purification | $4.88 \times 10^8$ | (113.6) | 0.35 | (1.0) | 0.21 | (0.24) | $1.40 \times 10^6$ | 114.5 |
| 4 | Extract of bacterial cell homogenate | $7.47 \times 10^8$ | (100) | 29.3 | (100) | 42.9 | (100) | $2.55 \times 10^4$ | 1.0 |
| | Fraction of chromatographic purification | $5.72 \times 10^8$ | (76.6) | 0.20 | (0.7) | 0.05 | (0.12) | $2.86 \times 10^6$ | 112.2 |

(a) Measured by Micro BCA Protein Assay (Pierce)
(b) Measured by Endospacy (Seikagaku Kogyo K. K.)

Example 3

(Gradient elution from Heparin Sepharose column)

A column (25 mm (i.d.)×140 mm) was packed with Heparin Sepharose CL-6B (Pharmacia) and equilibrated with 0.02 M phosphate buffer (pH 8.0; specific electric conductivity, around 3 mS/cm). A cell extract of Bb strain S611 (420 mg of a total protein) was applied to the column. And then, the column was washed with the above buffer to wash out debris. Then, a gradient elution was carried out with a phosphate buffer (pH 8.0; specific electric conductivity, around 3 to 46 mS/cm) supplemented with 0 to 0.5 M sodium chloride to give a fraction containing dermonecrotic toxin with 24 mg of a total protein. A rate of recovery of dermonecrotic toxin was 40.8% and a purification degree (specific activity of purified dermonecrotic toxin fraction/specific activity of an extract of bacterial cell homogenate) was as high as 7.0. The analytical results are shown in Table 2.

Example 4

(Gradient elution from SP-Toyopearl 650M column)

A column (50 mm (i.d.)×140 mm) was packed with SP-Toyopearl 650M column (manufactured by Toso K. K.) and equilibrated with 0.02 M phosphate buffer (pH 8.0; specific electric conductivity, around 3 mS/cm). A cell extract of Bb strain S611 (631 mg of a total protein) was applied to the column. And then, the column was washed with the above buffer to wash out debris. Then, a gradient elution was carried out with a phosphate buffer (pH 8.0; specific electric conductivity, around 3 to 46 mS/cm) supplemented with 0 to 0.5 M sodium chloride to give a fraction containing dermonecrotic toxin with 2 mg of a total protein. A rate of recovery of dermonecrotic toxin was 11.5% and a purification degree (specific activity of purified dermonecrotic toxin fraction/specific activity of an extract of bacterial cell homogenate) was as high as 35.5. The analytical results are shown in Table 2.

TABLE 2

| No. | | Total BbT activity (MND) | (Rate of recovery) | Total protein (a) (mg) | (Rate of recovery) | Total endotoxin (b) (μg) | (Rate of recovery) | Specific activity (MND/mg protein) | Purification degree |
|---|---|---|---|---|---|---|---|---|---|
| Ex. 3 | Extract of bacterial cell homogenate | $1.12 \times 10^7$ | (100) | 421.5 | (100) | 1,820 | (100) | $2.7 \times 10^4$ | 1.0 |
| | Fraction of Heparin Cepharose CL-6B purification | $4.57 \times 10^6$ | (40.8) | 24.0 | (5.7) | 8.9 | (0.49) | $1.9 \times 10^5$ | 7.2 |
| Ex. 4 | Extract of bacterial cell homogenate | $1.98 \times 10^7$ | (100) | 631.0 | (100) | N.T.(c) | | $3.1 \times 10^4$ | 1.0 |
| | Fraction of SP-Toyopearl purification | $2.27 \times 10^6$ | (11.5) | 2.0 | (0.32) | N.T. | | $1.1 \times 10^6$ | 35.5 |

(a) Measured by Micro BCA Protein Assay (Pierce)
(b) Measured by Endospacy (Seikagaku Kogyo K. K.)
(c) Not tested Example 5

(Purification with high purity)

Figure 2:
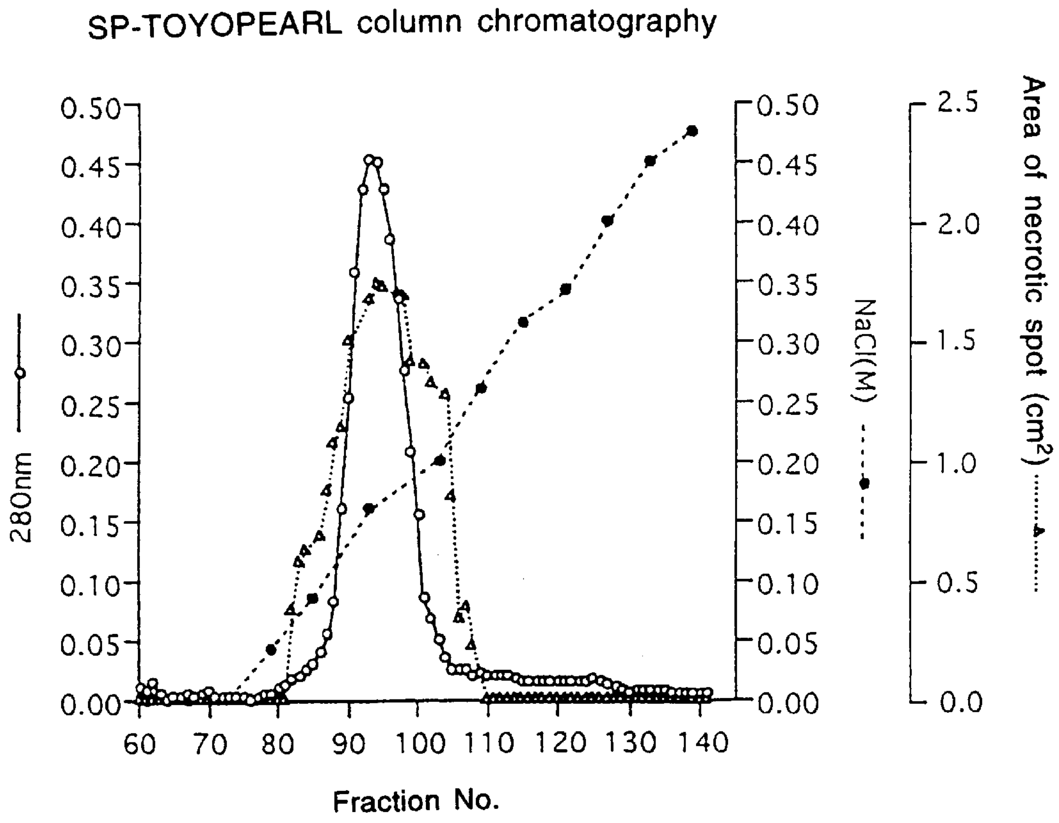
FIG. 2 shows a chromatogram in one step of a method for purifying dermonecrotic toxin according to the present invention.
Figure 3:
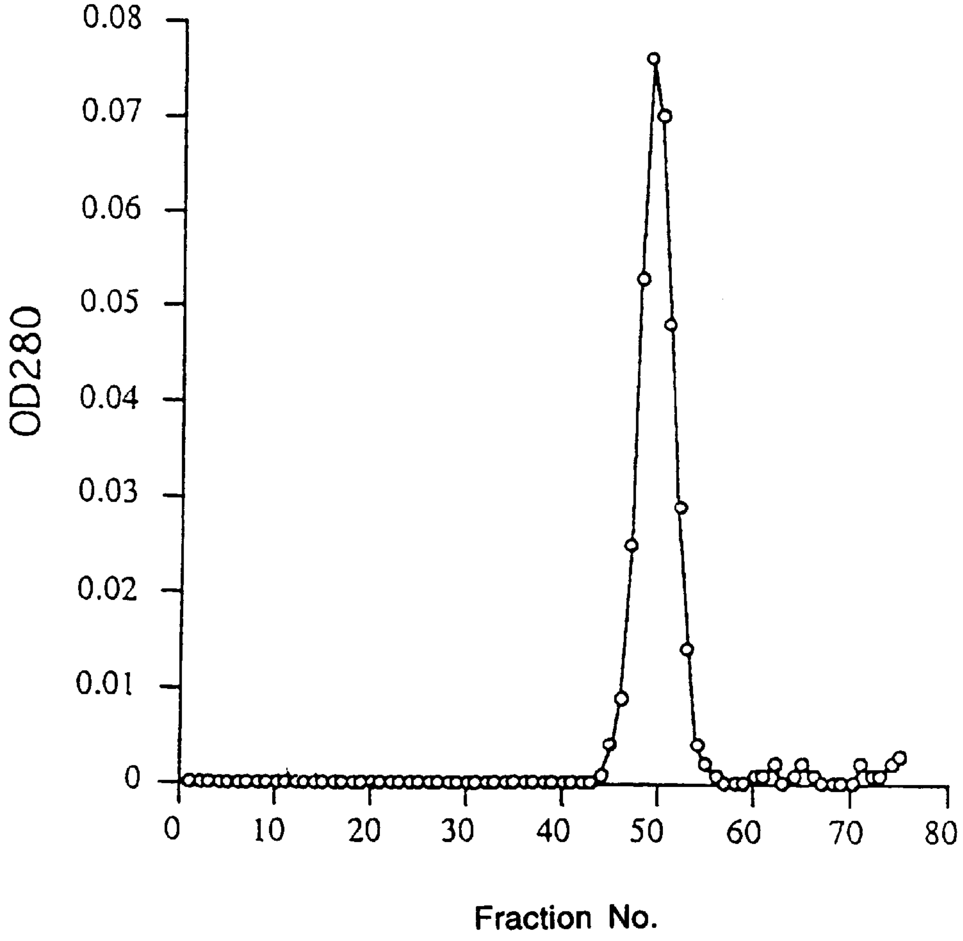
FIG. 3 shows a chromatogram in one step of a method for purifying dermonecrotic toxin according to the present invention.
Figure 4:
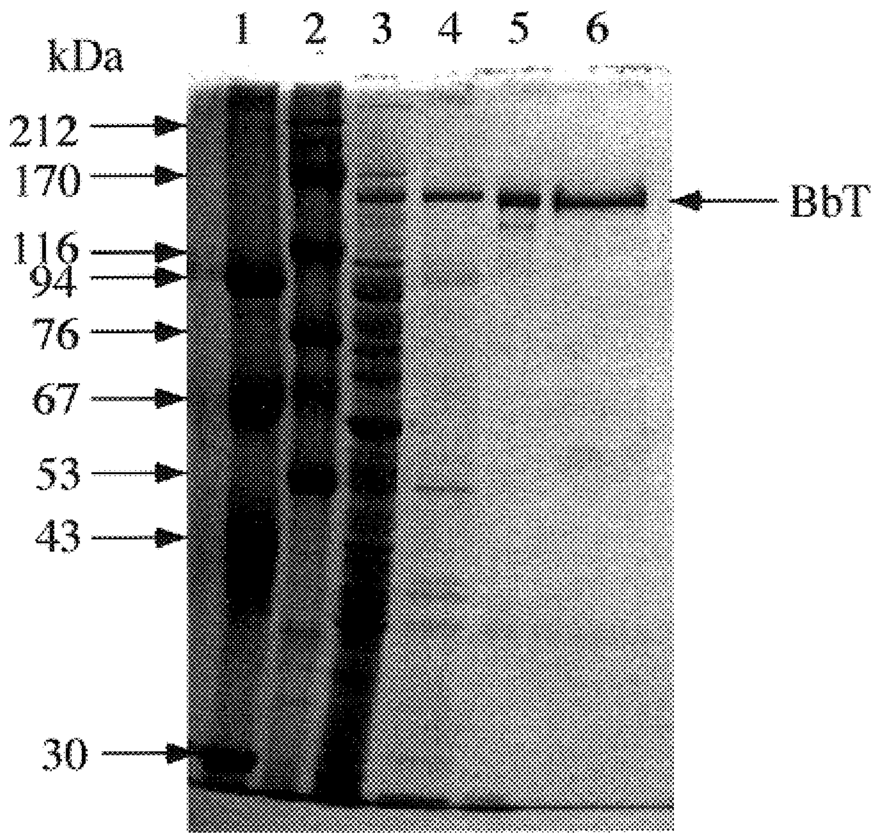
FIG. 4 shows results of analysis of a dermonecrotic toxin fraction obtained by a method for purifying dermonecrotic toxin according to the present invention.

A fraction of cellulose sulfate ester gel purification prepared as in Example 1 was dialyzed against 33 mM citrate/66 mM disodium hydrogenphosphate/1 M urea (pH 5.0). The dialyzate (9.1 mg of a total protein) was applied to SP-Toyopearl 650M (manufactured by Toso K. K.; 10 mm (i.d.)×80 mm) equilibrated with the same buffer, followed by washing with the same buffer to wash out debris. Then, a gradient elution was carried out with the above buffer supplemented with 0 to 0.5 M sodium chloride to give a fraction (SP fraction) containing dermonecrotic toxin (3.1 mg of a total protein). The SP fraction was further purified by a high performance liquid chromatography (HPLC) on TSK-gel G3000 SW column (21 mm (i.d.)×600 mm) equilibrated with 50 mM phosphate buffer (pH 7.1)/0.3 M sodium sulfate/1M urea, to give a fraction (HPLC fraction) containing dermonecrotic toxin (1.3 mg of a total protein). These chromatograms were shown in FIGS. 1 to 3, respectively. The analytical results of the extract of bacterial cell homogenate and fractions of dermonecrotic toxin were shown in Table 3 and FIG. 4 and properties of the purified toxin were listed in Table 4.

TABLE 3

| Purification Steps | Total BbT activity (MND) | (Rate of recovery) | Total protein (a) (mg) | (Rate of recovery) | Specific activity (MND/mg protein) | Purification degree |
|---|---|---|---|---|---|---|
| Extract of bacterial cell homogenate | $1.7 \times 10^7$ | (100) | 731 | (100) | $1.9 \times 10^4$ | 1 |
| Cellulose sulfate ester | $5.6 \times 10^6$ | (39.6) | 9.1 | (1.2) | $6.1 \times 10^5$ | 32 |
| S P Toyopearl | $6.2 \times 10^6$ | (44.3) | 3.1 | (0.4) | $2.0 \times 10^6$ | 105 |
| TSK G3000SW | $5.6 \times 10^6$ | (40.0) | 1.3 | (0.2) | $4.3 \times 10^6$ | 226 |

(a) According to BCA Protein Assay (manufactured by Pierce).

TABLE 4

| | |
|---|---|
| Molecular weight | 146 kDa |
| Minimum dermonecrotic dose | 0.23 ng |
| Minimum amount of splenoatrophy | 0.07 ng |
| 50% Lethal dose in mice | 3.8 ng |

Example 6

(Reduction of toxicity)

To each dermonecrotic toxin fraction prepared as in Examples 1 to 5 was added formalin and the reaction was carried out at 37 to 40° C. for 3 to 14 days for reduction of toxicity. To dermonecrotic toxin fraction was added 3/100 equivalent of 10% formalin, followed by the same amount on the next day and 2/100 equivalent on the day after the next day. After completing reduction of toxicity, the fraction was dialyzed against a phosphate-buffered saline.

Example 7

(Addition of adjuvant)

To the detoxified dermonecrotic toxin prepared as in Example 6 was added aluminum hydroxide gel and a preservative (thimerosal or formalin).

Example 8

(Potency test in mice)

Figure 5:
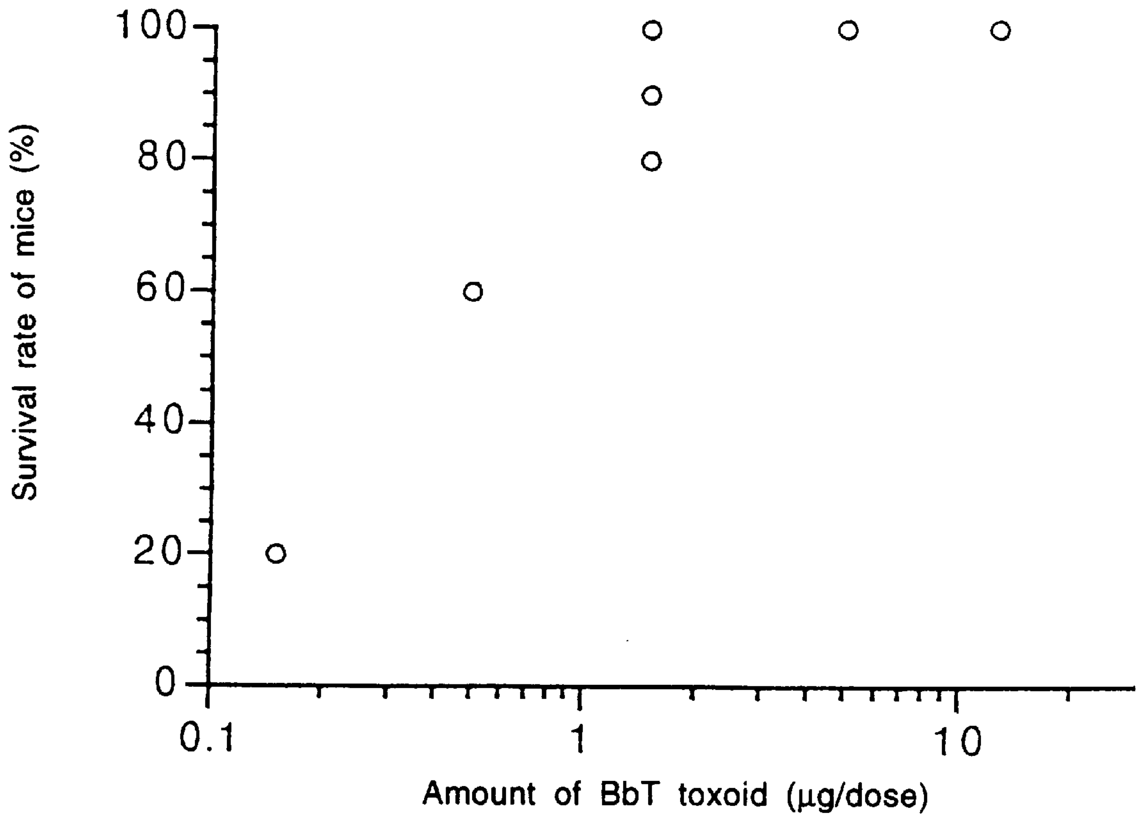
FIG. 5 shows results of a potency test in mice of a toxoid obtained according to the present invention.

Each 0.5 ml of the toxoid obtained as in Example 7 was intraperitoneally injected to ddY mice of 5 weeks old twice at an interval of 2 weeks. Two weeks after the final immunity, the animals were challenged intraperitoneally with about 50 (25 to 100) $LD_{50}$ of dermonecrotic toxin and survival was observed for 7 days. The results were shown in FIG. 5. There were positive correlation between a dose of toxoid and a rate of survival in mice.

Example 9

(Safety test in breeding pigs)

The fraction obtained as in Example 2 was subjected to detoxication as in Example 6. The toxoid (2 to 50 μg/2 ml/dose) supplemented with aluminum hydroxide gel was prepared as in Example 7 and injected intramuscularly to SPF pigs of 10 weeks old twice at an interval of 3 weeks. No clinical symptoms or abnormality in body temperature due to injection was observed in any of tested pigs.

Example 10

(Efficacy test in pregnant sow)

Figure 6:
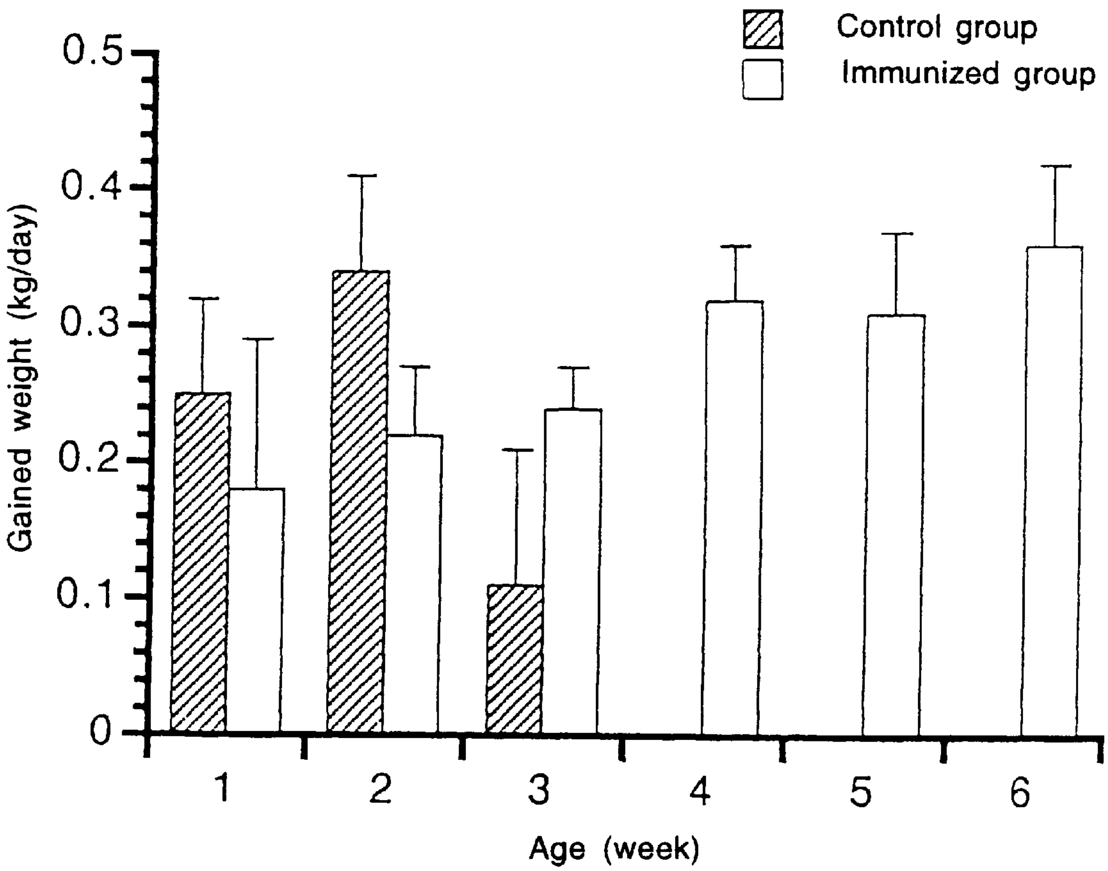
FIG. 6 shows results of an efficacy test in pregnant sow of a toxoid obtained according to the present invention.

The HPLC fraction obtained as in Example 5 was subjected to reduction of toxicity as in Example 6. The toxoid (25 μg/ml) supplemented with aluminum hydroxide gel was prepared as in Example 7 and each 2 ml was injected intramuscularly to a pregnant sow twice, 6 weeks and 3 weeks prior to farrowing. Control sows were injected with a placebo vaccine. All the progenies fed on sufficient colostrum were challenged intranasally with $2\times10^8$ viable cells of Bb strain S611 at 3 days old and the half of the progenies was further challenged intramuscularly with 2600 MND dermonecrotic toxin twice, at 2 and 3 weeks old. The obtained titer of dermonecrotic toxin neutralizing antibody was shown in Table 5. The titer of BbT neutralizing antibody was 32 in blood and 256 in colostrum of sow on farrowing, and the titer of maternal antibody in progeny was 128. The maternal antibody continued to be positive for more than 6 weeks. A sow with placebo injection and progeny thereof were seronegative. The results of the challenge test are shown in Table 6. The turbinate atrophy was detected in nine among 12 control pigs at the score of +to +++ but not in the immunized group. There was no distinction of intranasal bacterial recovery between both groups. As to a gained weight, there was difference in between both groups when challenged with dermonecrotic toxin in addition to Bb live bacteria as shown in FIG. 6. Upon the first challenge with dermonecrotic toxin at the 2 weeks old age, the gained weight ratio of the control group was reduced to about 1/3 of that of the immunized group, and as a result of the second challenge (at the 3 weeks old age), all the pigs in the control group died.

TABLE 5

| Test group | Antibody titer of sow (a) | | Titer of maternal antibody in piglets of various weeks old | | | | | | | | | | | |
|---|---|---|---|---|---|---|---|---|---|---|---|---|---|---|
| | Serum | Colostrum | 0 | | | 2 | | | 4 | | | 6 | | |
| Immunized | 32 | 256 | 128 | 128 | 128 | 64 | 64 | 32 | 16 | 32 | 32 | 16 | 16 | 32 |
| | | | 128 | 128 | | 64 | 64 | | 32 | 32 | | 16 | 16 | |
| Control | <1 | <1 | <1 | <1 | <1 | <1 | <1 | <1 | <1 | <1 | <1 | <1 | <1 | <1 |
| | | | <1 | <1 | <1 | <1 | <1 | <1 | <1 | <1 | <1 | <1 | <1 | <1 |

(a) at delivery

TABLE 6

| Group | Pig No. | Challenge with Bb | Challenge with BbT | Turbinate atrophy | Bacterial recovery (a) | Note |
|---|---|---|---|---|---|---|
| Immunized | Y126 | + | − | −/− b) | ++++ | |
| | Y127 | + | − | −/− | + | |
| | Y128 | + | − | −/− | ++++ | |
| | Y129 | + | − | −/− | ++++ | |
| | Y130 | + | + | −/− | + | |
| | Y131 | + | + | −/− | ++++ | |
| | Y132 | + | + | −/− | ++++ | |
| | Y133 | + | + | −/− | + | |
| | Y134 | + | + | −/− | ++++ | |
| Control | Y151 | + | − | +/+ | +++ | |
| | Y152 | + | − | −/+ | ++++ | |
| | Y153 | + | − | −/+ | ++++ | |
| | Y154 | + | − | ++/+ | ++++ | |
| | Y155 | + | − | +/+ | + | |
| | Y156 | + | − | −/− | ++++ | |
| | Y157 | + | + | +++/++ | NT c) | Died at 2nd day d) |
| | Y158 | + | + | +++/+++ | NT | Died at 2nd day |
| | Y159 | + | + | +++/++ | NT | Died at 6th day |
| | Y160 | + | + | +++/++ | NT | Died at 5th day |
| | Y161 | + | + | ++/++ | NT | Died at 1st day |
| | Y162 | + | + | +/+ | NT | Died at 3rd day |

a) Colony number appeared on plate culture smeared with intranasal swab; −: 0, +: ~50, ++: ~100, +++: ~200, ++++:200~
b) Assessed by five-grade (− to ++++); score of left turbinate bone/right turbinate bone
c) Not tested
d) Number of days counted from the second BbT challenge Example 11

(Efficacy test in breeding pigs)

The fraction obtained as in Example 2 was subjected to reduction of toxicity as in Example 6. The toxoid (2 to 50 μg/2 ml/dose) supplemented with aluminum hydroxide gel was prepared as in Example 7 and was injected intramuscularly twice at an interval of 3 weeks to SPF pigs of 10 weeks old. Four weeks after the final immunity, the pigs were intranasally challenged with $2\times10^8$ live Bb bacteria and a titer of dermonecrotic toxin neutralizing antibody was tested until 3 weeks after the challenge. As shown in Table 7, the control pigs remained seronegative for a BbT neutralizing antibody even after the challenge. On the other hand, all the pigs in the immunized group were converted to seropositive for a BbT neutralizing antibody. The immunized pigs injected with 2 or 6 μg/2 ml/dose of toxoid showed a radical increase in the neutralizing antibody after the challenge whereas those injected with 20 or 50 μg/2 ml/dose did not.

It has been reported that dermonecrotic toxin has an antibody production-inhibiting activity (Sekiya, K., Microbiol. Immunol., 27, p.905–915 (1983)). The reason why the control pigs do not show increase in a neutralizing antibody after the challenge appears to be due to the immunosuppressive activity of BbT produced by the challenging bacteria. Accordingly, since the radical increase in the neutralizing antibody in the immunized group is due to protection from the antibody production-inhibiting activity of BbT, it was suggested that 2 μg of BbT toxoid is effective in breeding pigs.

TABLE 7

| a) A dose of | b) | Titer of BbT neutralizing antibody at various weeks after the first immunization | | | | | | Titer of Bb-aggluting antibody at various weeks after the first immunization | | | | Intranasal bacterial |
|---|---|---|---|---|---|---|---|---|---|---|---|---|
| BbT content | Pig No. | 0 | 3 | 4 | 5 | 7 | 10 | 0 | 3 | 7 | 10 | recovery |
| 0 | Y135 | <1 | <1 | <1 | <1 | <1 | <1 | <10 | <10 | <10 | 40 | ++ |
| | Y136 | <1 | <1 | <1 | <1 | <1 | <1 | <10 | <10 | <10 | 80 | ++++ |
| 2 | Y137 | <1 | <1 | 16 | 8 | 8 | 128 | <10 | <10 | <10 | 640 | +++ |
| | Y138 | <1 | <1 | 16 | 32 | 16 | 512 | <10 | <10 | <10 | 1280 | +++ |
| | Y139 | <1 | <1 | 8 | 16 | 16 | 1024 | <10 | <10 | <10 | 80 | ++++ |
| 6 | Y140 | <1 | <1 | 16 | 32 | 16 | 512 | <10 | <10 | <10 | 640 | +++ |
| | Y141 | <1 | <1 | 16 | 64 | 16 | 128 | <10 | <10 | <10 | 320 | – |
| | Y142 | <1 | <1 | 64 | 64 | 32 | 64 | <10 | <10 | <10 | 160 | ++++ |
| 20 | Y143 | <1 | <1 | 32 | 64 | 64 | 32 | <10 | <10 | <10 | 640 | ++++ |
| | Y144 | <1 | <1 | 4 | 8 | 8 | 1 | <10 | <10 | <10 | 40 | + |
| | Y145 | <1 | <1 | 16 | 32 | 8 | 8 | <10 | <10 | <10 | 320 | ++ |
| 50 | Y146 | <1 | <1 | 64 | 64 | 64 | 64 | <10 | <10 | <10 | 1280 | +++ |
| | Y147 | <1 | <1 | 128 | 128 | 64 | 32 | <10 | <10 | <10 | 320 | + |
| | Y148 | <1 | <1 | 64 | 256 | 64 | 64 | <10 | <10 | <10 | 640 | ++ |

a) μg/2 ml/dose
b) SPF pigs of 10 weeks old were intramuscularly injected with BbT toxoid twice at 0 and 3 weeks and challenged intranasally with live Bb at 7 week.

Preparation 4

(Extract from disrupted bacterial cells: BbT toxoid 1)

Bb strain S611 was cultured in a peptone medium in fermentor with aeration at 37° C. for 24 hours. The bacterial cells were concentrated by centrifugation and then mechanically disrupted. To a solution (crude BbT fraction) obtained after removing debris by centrifugation or membrane filtration (pore size: 0.45 μm) was added formalin at a final concentration of 0.8% and the toxicity was reduced at 37 to 40° C. for 7 days. The obtained toxoid was dialyzed against a phosphate-buffered saline. To the dialyzed product was added aluminum hydroxide gel at 1 mg (as an amount of aluminum)/ml to give BbT toxoid 1.

Preparation 5

(BbT toxoid 2)

The crude BbT fraction obtained as in Preparation 4 was purified by chromatography on a cellulose sulfate ester gel column. The crude BbT was applied to a cellulose sulfate ester gel equilibrated with 20 mM phosphate buffer (pH 8.0) and the gel was washed with the same buffer. BbT was eluted from a cellulose sulfate ester gel column (7.8 cm (i.d.)×45 cm) with 20 mM phosphate buffer (pH 8.0) supplemented with 1.5 M NaCl and 1 M urea. The eluted fraction (CS1 fraction) was subjected to the detoxication procedure as in Preparation 4, and after dialysis, aluminum hydroxide gel was added to give BbT toxoid 2.

Preparation 6

(BbT toxoid 3)

The CS1 fraction obtained as in Preparation 5 was further purified by a TSK gel HW65 (2.64 cm (i.d.)×69 cm) and HW75 (2.64 cm (i.d.)×64 cm) combination column. The CS1 fraction was passed through the column equilibrated with 0.05 M phosphate buffer (pH 7.2) supplemented with 0.3 M sodium sulfate and 1 M urea and fractionated with the same buffer, and then fractions containing the dermonecrotic toxin activity were pooled. The pooled fraction was subjected to the detoxication procedure as in Preparation 4, and after dialysis, aluminum hydroxide gel was added to give BbT toxoid 3.

Preparation 7

(BbT toxoid 4)

The crude BbT fraction obtained as in Preparation 4 was purified by chromatography on a cellulose sulfate ester gel column. The crude BbT was applied to a cellulose sulfate ester gel equilibrated with 20 mM phosphate buffer (pH 8.0) supplemented with 0.1 M NaCl and the gel was washed with the same buffer. BbT was eluted from a cellulose sulfate ester gel with 20 mM phosphate buffer (pH 8.0) supplemented with 0.5 M NaCl. The eluted fraction (CS2 fraction) was subjected to the detoxication procedure as in Preparation 4, and after dialysis, aluminum hydroxide gel was added to give BbT toxoid 4.

Preparation 8

(BbT toxoid 5)

The CS2 fraction obtained as in Preparation 7 was further purified by Affi-gel blue column (manufactured by BioRad; 100–200 mesh; 5.0 cm (i.d.)×17 cm). The CS2 fraction dialyzed against 50 mM Tris buffer (pH 7.5) was applied to Affigel blue column equilibrated with the same buffer and the column was washed with 50 mM Tris buffer (pH 7.5) supplemented with 1 M disodium hydrogenphosphate. After the column was washed further with 50 mM Tris buffer (pH 7.5), BbT was eluted with 50 Mm Tris buffer (pH 7.5) supplemented with 2 M magnesium chloride and 1 M urea. This fraction was subjected to the detoxication procedure as in Preparation 4, and after dialysis, aluminum hydroxide gel was added to give BbT toxoid 5.

Preparation 9

(BbT antitoxin)

The highly purified BbT fractions obtained as in Examples 1 and 5 were subjected to the detoxication procedure as in Preparation 4, and after dialysis, aluminum hydroxide gel was added to give BbT toxoid 6. Each 1 ml of this toxoid was inoculated 8 times over 3 months to SPF pigs of 27 weeks old to give BbT antitoxin (a neutralization titer, 4,096; a titer of agglutinating antibody, <20).

Preparation 10

(PmT toxoid)

Toxigenic Pm type D strain of S70 were cultured in a Heart infusion broth in fermentor with aeration at 37° C. for 24 hours. The bacterial cells were concentrated by centrifugation and then mechanically disrupted. A solution (abbreviated as "crude PmT") obtained after removing debris by centrifugation or membrane filtration (pore size: 0.45 μm) was purified by an anion exchange chromatography. The crude PmT was applied to the anion exchanger equilibrated with a neutral phosphate buffer supplemented with 0 to 0.3 M NaCl or Tris buffer and the exchanger was washed with the same buffer. PmT was eluted from the exchanger with the same buffer supplemented with 0.4 to 0.5 M NaCl. To this partially purified PmT fraction was added formalin at 0.4% and the toxicity was reduced at 37° C. for 14 or more days. The obtained toxoid was dialyzed against a phosphate-buffered saline. To the dialyzate was added aluminum hydroxide gel at 1 mg Al/ml to give PmT toxoid.

Example 12

(Immunogenicity in guinea pig of BbT toxoids obtained by various purification procedures)

Each 0.5 ml of the BbT toxoids with 3,000 MND/ml (activity prior to detoxication) obtained as in Preparations 4 to 8 was intramuscularly injected to guinea pigs (Hartely; female; 5 weeks old) at the thigh. The animals were bled 28 days after the injection and the titer of a BbT neutralizing antibody was tested. Measurement of the neutralizing antibody was carried out by a two-fold serial dilution of inactivated serum with a phosphate-buffered saline. To the diluted serum was added an equal amount of BbT (titer; 4 MND/0.1 ml), and after reaction under ice-cooling overnight, each 0.1 ml of the mixture was subcutaneously injected to guinea pigs. Measurement was made one day after the injection wherein the neutralization titer was shown as a maximum dilution of serum (dilution fold of serum) which inhibited the dermonecrotic reaction.

As shown in Table 8, guinea pigs injected with BbT toxoids 1 and 2 having $1.4\times10^4$ MND/mg protein of a specific activity remained seronegative for a neutralizing antibody. In case of guinea pigs injected with BbT toxoid 3 having $3.7\times10^4$ MND/mg protein of a specific activity, 2 among 3 guinea pigs were seropositive, and all the animals were converted to seropositive with BbT toxoid injection of more than $7.8\times10^4$ MND/mg protein of a specific activity.

BbT is apt to be insolubilized during purification and has properties to easily form a complex with bacterially derived materials such as lipids, acid proteins, etc. (Wordlaw, A. C. and Parton, R., Parmacol. Ther., 19, p.1–53 (1983)). Accordingly, it appears that reduction of these bacterially derived materials enables more sufficient detoxication or reduces masking of immunogenic epitope(s) on the BbT molecule so that efficiency of antigen presentation is enhanced to thereby increase the immunogenicity of BbT toxoid.

TABLE 8

| BbT Toxoid | Specific activity (MND/mg protein) | Titer of dermonecrotic toxin neutralizing Ab. | | |
|---|---|---|---|---|
| 1 | 14000 | <2 | <2 | <2 |
| 2 | 14000 | <2 | <2 | <2 |
| 3 | 37000 | <2 | 2 | 4 |
| 4 | 76000 | 32 | 32 | 128 |
| 5 | 96000 | 8 | 32 | 32 |
| Killed vaccine (Manufactured by A) | — | <2 | <2 | <2 |
| Killed vaccine (Manufactured by B) | — | <2 | <2 | <2 |

Each toxoid was adjusted to 3,000 MND/ml with addition of aluminum hydroxide gel at 1 mg Al/ml.

Example 13

(Protection line by BbT neutralizing antibody)

SPF pigs of 2 days old were passively immunized by intraperitoneal injection of 0.2, 1.0, 2.0 or 20 ml of BbT antitoxin obtained in Preparation 10. The pigs were intranasally challenged at 3 days old with $10^8$ CFU of Bb strain S611 and further intramuscularly challenged at 7 days old with the crude BbT (1,940 MND/head). As shown in FIGS. 7A and 7B, protection was observed at a BbT neutralizing antibody titer of more than 1 against the lethal activity of BbT, whereas protection was possible with more than 4 against the dermonecrotic activity.

Example 14

(Protection line by PmT neutralizing antibody)

The crude PmT toxoid obtained as in Preparation 10 was emulsified with an equal amount of Freund's incomplete adjuvant. Eight SPF pregnant sows were divided into an immunization group consisting of 6 sows and a control group of 2 sows. For the immunization group, each 3 ml of toxoid (840 MND/ml) was intramuscularly injected 2 to 5 times to pigs during pregnancy. After farrowing, progeny was fed on sufficient colostrum and intramuscularly challenged at 2 or 9 days old with 20 to 160 MND of the crude PmT. The piglets were observed for 14 days after challenge and the lesion in the turbinate was checked. As shown in Table 9, protection was observed against the turbinate atrophic activity of PmT at the PmT neutralizing antibody titer of more than 2 whereas protection was possible against the lethal activity even at less than 2.

TABLE 9

| Test class | Titer of PmT neutralizing antibody a) | Death No./ Total No. b) | Score of mean turbinate atrophy c) |
|---|---|---|---|
| Immunized | 128 | 0/2 | 0 |
| | 64 | 0/2 | 0 |
| | 32 | 0/3 | 0 |
| | 16 | 0/5 | 0 |
| | 4 | 0/1 | 0 |
| | 2 | 0/9 | 0 |
| | <2 | 0/10 | 2.4 |
| Control | <2 | 3/14 | 2.3 |

a) Titer of maternal antibody at challenge measured with embryonated bovine lung cells.
b) Piglets of 2 or 9 days void were intramuscularly challenged at the thigh with 20 to 160 MND PmT.
c) Mean value of score of turbinate atrophy; 0: normal, 1: slight, 2: moderate, 3: severe, 4: extremely severe Example 15

(Test of Bb and Pm challenge in pigs passively immunized with BbT antitoxin)

SPF pigs of 2 days old were passively immunized by intraperitoneal injection of 20 ml of BbT antitoxin obtained in Preparation 10. The pigs were intranasally challenged at 3 and 7 days old with $10^8$ CFU of Bb strain S611 and $10^8$ CFU of Pm type D strain of S70, respectively, and necropsy was carried out at 6 weeks old. As shown in Table 10, a large quantity of Bb was recovered from the nasal mucosa when immunized with BbT antitoxin whereas recovery of Pm was much lowered in comparison with control. The turbinate lesion in the control group was assessed as sever (+++) to extreme sever (++++) whereas in the immunized group, one pig was normal (–) and the others were sever and extreme sever, showing a great variance for from individual to individual.

TABLE 10

| Group | Piglet No. | Piglet Sex | Titer of BbT neutralizing antibody at various days old 3 | 7 | 15 | 30 | 44 | Titer of PmT neutralizing antibody at various days old* 3 | 7 | 15 | 30 | 44 | Turbinate atrophy | Intranasal bacterial recovery Bb | PmD |
|---|---|---|---|---|---|---|---|---|---|---|---|---|---|---|---|
| Immunized a) | Y89 | ♀ | 256 | NT | 64 | 32 | 16 | <2 | NT | <2 | <2 | <2 | ++++ | ++++ | ++ |
| | Y100 | ♀ | 256 | 128 | 64 | 32 | 64 | <2 | <2 | <2 | <2 | <2 | – | ++++ | – |
| | Y125 | ♂ | 256 | 128 | 64 | 32 | 32 | <2 | <2 | <2 | <2 | <2 | +++ | ++++ | – |
| Control | Y80 | ♂ | <1 | NT | <1 | <1 | <1 | <2 | NT | <2 | <2 | <2 | ++++ | ++++ | ++++ |
| | Y83 | ♀ | <1 | NT | <1 | <1 | <1 | <2 | NT | <2 | <2 | <2 | +++ | ++++ | ++++ |
| | Y99 | ♀ | <1 | <1 | <1 | <1 | <1 | <2 | <2 | <2 | <2 | <2 | ++++ | ++++ | ++++ |

a) Swine anti-BbT antiserum was intraperitoneally injected to piglets of 2 days old.
*Piglets were intranasally challenged with Bb S611 bacteria (10^8 CFU/head) at 3 days old and with PmD S70 bacterial (10^8/head) at 7 days old.

Dermonecrotic toxin is produced within the bacterial cells and secreted out of the cells by bacterial lysis. Accordingly, BbT antitoxin cannot block Bb colonization on the nasal mucosa. For Pm colonization, Bb should have previously caused the lesion at the mucosa. As a factor produced by Bb causing the lesion in the nasal mucosa, BbT (Elias, B. et al., Jpn. J. Vet. Sci., 52, p.677–688 (1990)) and a tracheal cytotoxin (Cookson, B. T. and Goldman, W. E., J. Cell. Biochem., 11B (Suppl.) p.124; Dugal, F. et al., Can. J. Vet. Res., 56, p.260–264 (1992)) are most important. Since a tracheal cytotoxin has an activity to terminate tracheal ciliary movement, an activity to destroy ciliary epithelial cells and an activity to accelerate mucus secretion, all the activities being important for colonization of Pm, immunization with BbT antitoxin can only partially block Pm colonization.

Viewing these facts, immunization against at least BbT and the tracheal cytotoxin should be established for blocking Pm colonization on the nasal mucosa. However, a tracheal cytotoxin toxoid is far from practical use, bearing many problems to be solved such as establishment of a process for purification, immunogenicity, yield, etc. Accordingly, for preventing primary symptoms of atrophic rhinitis while obviating an economical loss, an AR inactivated vaccine should comprise at least a toxoid mixture of dermonecrotic toxin.

Example 16

(Example of toxoid mixture)

To the detoxified BbTs obtained as in Examples 2 and 6 was added aluminum hydroxide gel and the mixture was stirred. A BbT toxoid stock solution was prepared by adjusting a concentration of BbT to 8,700 to 220,000 MND/ml (equivalent to 2 to 50 gg/ml BbT protein prior to detoxication) and a concentration of aluminum to 0.5 to 2.5 mg/ml and adding a preservative.

A PmT stock solution was prepared by preparing the detoxified PmT supplemented with aluminum hydroxide gel obtained as in Preparation 11 at 3,400 MND/ml (amount of toxin prior to detoxication) or more and adding a preservative thereto. The used preservative was 0.01% thimerosal or 0.1 to 0.4% formalin. Each equal amount of the BbT stock solution and the PmT toxoid stock solution were mixed together to give a toxoid mixture.

Each 2 ml of the toxoid mixture was intramuscularly inoculated to the neck of SPF pigs of 9 weeks old twice at an interval of 3 weeks. Serum was taken with the lapse of time and titers of a BbT neutralizing antibody and a PmT neutralizing antibody were measured. A titer of PmT neutralizing antibody was measured by a neutralization test using embryonated bovine lung cells (Rutter, J. M. and Luther, P. D., Vet. Rec., 114, p.393–396 (1984)). Table 11 shows titers of neutralizing antibodies in pigs whereas Table 12 shows results of a titer test in mice. No distinction was observed in immunogenicity between each plain toxoid of BbT and PmT and the toxoid mixture when administered to pigs and mice, and the toxoid mixture exhibited a response of neutralizing antibodies sufficient for protection and was safe enough.

TABLE 11

| Test group a) | Pig No. | Titer of BbT neutralizing antibody at various days after the first immunization 0 | 10 | 21 | 35 | 50 | 64 | Titer of PmT neutralizing antibody at various days after the first immunization 0 | 10 | 21 | 35 | 50 | 64 |
|---|---|---|---|---|---|---|---|---|---|---|---|---|---|
| BbT alone | Y117 | <1 | <1 | <1 | 32 | 32 | 8 | <2 | <2 | <2 | <2 | <2 | <2 |
| | Y118 | <1 | <1 | <1 | <1 | <1 | <1 | <2 | <2 | <2 | <2 | <2 | <2 |
| | Y119 | ’11 | <1 | <1 | 64 | 16 | 8 | <2 | <2 | <2 | <2 | <2 | <2 |
| Toxoid mixture | Y120 | <1 | <1 | <1 | 64 | 32 | 16 | <2 | <2 | <2 | 256 | 128 | 128 |
| | Y121 | <1 | <1 | <1 | 16 | 8 | 4 | <2 | <2 | <2 | 64 | 32 | 16 |
| | Y122 | <1 | <1 | <1 | 2 | 2 | <1 | <2 | <2 | <2 | 64 | 32 | 32 |
| PmT alone | Y123 | <1 | <1 | <1 | <1 | <1 | <1 | <2 | <2 | <2 | 64 | 32 | 16 |
| | Y124 | <1 | <1 | <1 | <1 | <1 | <1 | <2 | <2 | <2 | 128 | 128 | 64 |
| | Y125 | <1 | <1 | <1 | <1 | <1 | <1 | <2 | <2 | <2 | 128 | 128 | 64 |
| Control | Y114 | <1 | <1 | <1 | <1 | <1 | <1 | <2 | <2 | <2 | <2 | <2 | <2 |
| | Y115 | <1 | <1 | <1 | <1 | <1 | <1 | <2 | <2 | <2 | <2 | <2 | <2 |
| | Y116 | <1 | <1 | <1 | <1 | <1 | <1 | <2 | <2 | <2 | <2 | <2 | <2 |

a) Each toxoid was injected intramuscularly at the neck on 0 and 21 days.

TABLE 12

| | BbT challenge | | PmT challenge | |
|---|---|---|---|---|
| Test group | Titer of BbT neutralization | Survival No./ Total No. | Titer of PmT neutralization | Survival No./ Total No. |
| BbT alone | 256 | 10/10 | N.T. | N.T. |
| PmT alone | N.T. | N.T. | 256 | 10/10 |
| BbT.PmT mixture | 512 | 9/10 | 1024 | 10/10 |
| Control | <1 | 0/10 | <2 | 0/10 |

Titer of neutralization as shown is that obtained at challenge.

What is claimed is:

1. A method for obtaining purified dermonecrotic toxin produced by bacteria of the species *Bordetella bronchiseptica,* the improvement comprising bringing a dermonecrotic toxin-containing solution into contact with a chromatographic gel sulfated by direct sulfation or a chromatographic gel to which a sulfated molecule is covalently bonded to thereby make the dermonecrotic toxin adsorbed on the chromatographic gel, and eluting the adsorbed dermonecrotic toxin from the chromatographic gel;

wherein said dermonecrotic toxin-containing solution is a *Bordetella bronchiseptica* bacterial cell extract prepared by subjecting *Bordetella bronchiseptica* cells to sonication, enzyme treatment, pressing, or freeze-thawing to produce a homogenate of *Bordetella bronchiseptica* cells and subjecting the resulting homogenate to centrifugation or membrane filtration to remove cellular debris.

2. A dermonecrotic toxin toxoid of *Bordetella bronchiseptica* which is deprived of toxin activity but retains immunogenicity, said toxoid being transformed from a purified dermonecrotic toxin by treatment with a chemical reagent, wherein said purified dermonecrotic toxin is prepared by bringing a solution containing dermonecrotic toxin produced by *Bordetella bronchiseptica* into contact with a chromatographic gel sulfated by direct sulfation or a chromatographic gel to which a sulfated molecule is covalently bonded to thereby adsorb the dermonecrotic toxin on the chromatographic gel and eluting the adsorbed dermonecrotic toxin from the chromatographic gel, and optionally further subjecting said purified dermonecrotic toxin to a purification procedure selected from the group consisting of dialysis, cation exchange chromatography, and gel filtration chromatography, wherein said dermonecrotic toxin-containing solution is a *Bordetella bronchiseptica* bacterial cell extract prepared by subjecting *Bordelella bronchiseptica* cells to sonication, enzyme treatment, pressing, or freeze-thawing, to produce a homogenate of *Bordetella bronchiseptica* cells and subjecting the resulting homogenate to centrifugation or membrane filtration to remove cellular debris.

3. The method for obtaining purified dermonecrotic toxin according to claim 1 wherein the chromatographic gel is selected from the group consisting of a cellulose sulfate ester and a polymer, wherein said polymer is bound to heparin, a sulfopropyl group, or a blue dye having a sulfone group within the molecule.

4. The method for obtaining purified dermonecrotic toxin according to claim 1 which comprises the steps:

(1) equilibrating the chromatographic gel sulfated by direct sulfation or the chromatographic gel to which a sulfated molecule is covalently bonded by previously treating the chromatographic gel with a buffer having pH 7 to 9 and a fixed specific electric conductivity ranging from 3 to 20 mS/cm, (2) bringing the dermonecrotic toxin-containing solution into contact with the chromatographic gel having a sulfate group as a ligand or the chromatographic gel sulfated by direct sulfation under conditions of pH 7 to 9, a temperature of 0 to 30° C., and a fixed specific electric conductivity ranging from 3 to 20 mS/cm, (3) washing the chromatographic gel with a buffer having pH 5 to 10 and a fixed specific electric conductivity ranging from 3 to 20 mS/cm prior to elution of dermonecrotic toxin from the chromatographic gel, and (4) eluting dermonecrotic toxin from the chromatographic gel by using a buffer having a pH of 5 to 10 and a specific electric conductivity of 20 mS/cm to 130 mS/cm;

wherein said dermonecrotic toxin-containing solution is a *Bordetella bronchiseptica* bacterial cell extract prepared by subjecting *Bordetella bronchiseptica* cells to sonication, enzyme treatment, pressing, or freeze-thawing, to produce a homogenate of *Bordetella bronchiseptica* cells and subjecting the resulting homogenate to centrifugation or membrane filtration to remove cellular debris.

5. The method for obtaining purified dermonecrotic toxin according to claim 4 which comprises the steps:

(1) equilibrating a chromatographic gel of a cellulose sulfate ester by previously treating the chromatographic gel with a buffer having pH 7 to 9 and a specific electric conductivity of 20 mS/cm or less, (2) bringing the dermonecrotic toxin-containing solution into contact with the chromatographic gel of a cellulose sulfate ester under conditions of pH 7 to 9, a temperature of 0 to 30° C., and a fixed specific electric conductivity of 20 mS/cm or less, (3) washing the chromatographic gel with a buffer having a pH of 5 to 10 and a specific electric conductivity of 20 mS/cm or less prior to elution of dermonecrotic toxin from the chromatographic gel, and (4) eluting dermonecrotic toxin from the chromatographic gel by using a buffer having a pH of 5 to 10 and a specific electric conductivity ranging from 22 to 130 mS/cm.

6. The method for obtaining purified dermonecrotic toxin according to claim 4 which comprises the steps:

(1) equilibrating a heparin-bound chromatographic gel by previously treating the chromatographic gel with a buffer having pH 7 to 9 and a specific electric conductivity ranging from 3 to 5 mS/cm, (2) bringing the dermonecrotic toxin-containing solution into contact with the heparin-bound chromatographic gel under conditions of pH 7 to 9, a temperature of 0 to 30° C., and a fixed specific electric conductivity ranging from 3 to 5 mS/cm, (3) washing the chromatographic gel with a buffer having a pH of 5 to 10 and a specific electric conductivity ranging from 3 to 5 mS/cm prior to elution of dermonecrotic toxin from the chromatographic gel, and (4) eluting dermonecrotic toxin from the chromatographic gel by using a buffer having a pH of 5 to 10 and a specific electric conductivity ranging from 3 to 130 mS/cm.

7. The method for purifying dermonecrotic toxin of claim 1 wherein the dermonecrotic toxin-containing solution is a culture or an extract of a microorganism or a cell which is transformed with an expression vector comprising a recombinant DNA containing a gene coding for dermonecrotic toxin of *Bordetella bronchiseptica* and which cell expresses said toxin.

8. The dermonecrotic toxin toxoid of claim 2 wherein said purified dermonecrotic toxin is prepared by a method comprising the steps:

(1) equilibrating the chromatographic gel sulfated by direct sulfation or the chromatographic gel to which a sulfated molecule is covalently bonded by previously treating the chromatographic gel with a buffer having pH 7 to 9 and a specific electric conductivity ranging from 3 to 20 mS/cm, (2) bringing the dermonecrotic toxin-containing solution into contact with the chromatographic gel sulfated by direct sulfation or the chromatographic gel to which a sulfated molecule is covalently bonded under conditions of pH 7 to 9, a temperature of 0 to 30° C., and a fixed specific electric conductivity ranging from 3 to 20 mS/cm, (3) washing the chromatographic gel with a buffer having a pH of 5 to 10 and a specific electric conductivity ranging from 3 to 20 mS/cm prior to elution of dermonecrotic toxin from the chromatographic gel, and (4) eluting dermonecrotic toxin from the chromatographic gel by using a buffer having a pH of 5 to 10 and a specific electric conductivity ranging from 20 to 130 mS/cm;

wherein said dermonecrotic toxin-containing solution is a *Bordetella bronchiseptica* cell extract prepared by subjecting *Bordetella bronchiseptica* cells to sonication, enzyme treatment, pressing, or freeze-thawing, to produce a homogenate of *Bordetella bronchiseptica* cells and subjecting the resulting homogenate to centrifugation or membrane filtration to remove cellular debris.

9. The dermonecrotic toxin toxoid of claim 2 which has at least a 37,500 minimum necrotic dose (MND)/mg protein prior to detoxification.

10. The dermonecrotic toxin toxoid of claim 9 which is adjusted to a concentration of at least 3000 MND/ml prior to detoxification.

11. A purified dermonecrotic toxin of *Bordetella bronchiseptica* having a specific activity of at least 37,000 MND/mg protein, said toxin being obtained by bringing a solution containing dermonecrotic toxin produced by *Bordetella bronchiseptica* into contact with a chromatographic gel sulfated by direct sulfation or a chromatographic gel to which a sulfated molecule is covalently bonded to thereby make the dermonecrotic toxin adsorbed on the chromatographic gel, and eluting the adsorbed dermonecrotic toxin from the chromatographic gel, and optionally further subjecting the resulting dermonecrotic toxin to a purification procedure selected from the group consisting of dialysis, cation exchange chromatography, and gel filtration chromatography, wherein said dermonecrotic toxin-containing solution is a *Bordetella bronchiseptica* bacterial cell extract prepared by subjecting *Bordetella bronchiseptica* cells to sonication, enzyme treatment, pressing, or freeze-thawing, to produce a homogenate of *Bordetella bronchiseptica* cells and subjecting the resulting homogenate to centrifugation or membrane filtration to remove cellular debris.

12. A purified dermonecrotic toxin of *Bordetella bronchiseptica* according to claim 11, wherein said toxin is prepared by the steps of:

(1) equilibrating a chromatographic gel sulfated by direct sulfation or a chromatographic gel to which a sulfated molecule is covalently bonded by previously treating the chromatographic gel with a buffer having pH 7 to 9 and a specific electric conductivity ranging from 3 to 20 mS/cm, (2) bringing the dermonecrotic toxin-containing solution into contact with the chromatographic gel having a sulfate group as a ligand or the chromatographic gel sulfated by direct sulfation under conditions of pH 7 to 9, a temperature of 0 to 30° C., and a fixed specific electric conductivity ranging from 3 to 20 mS/cm, (3) washing the chromatographic gel with a buffer having a pH of 5 to 10 and a specific electric conductivity ranging from 3 to 20 mS/cm prior to elution of dermonecrotic toxin from the chromatographic gel, and (4) eluting dermonecrotic toxin from the chromatographic gel by using a buffer having a pH of 5 to 10 and a specific electric conductivity ranging from 20 to 130 mS/cm.

13. A purified dermonecrotic toxin of *Bordetella bronchiseptica* according to claim 11, wherein said toxin is prepared by the steps of:

(1) equilibrating a chromatographic gel of a cellulose sulfate ester by previously treating the chromatographic gel with a buffer having pH 7 to 9 and a specific electric conductivity of 20 mS/cm or less, (2) bringing the dermonecrotic toxin-containing solution into contact with the chromatographic gel of a cellulose sulfate ester under conditions of pH 7 to 9, a temperature of 0 to 30° C., and a specific electric conductivity of 20 mS/cm or less prior to elution of dermonecrotic toxin from the chromatographic gel, (3) washing the chromatographic gel with a buffer having a pH of 5 to 10 and a specific electric conductivity ranging from 3 to 20 mS/cm prior to elution of dermonecrotic toxin from the chromatographic gel, and (4) eluting dermonecrotic toxin from the chromatographic gel by using a buffer having a pH of 5 to 10 and a specific electric conductivity ranging from 20 to 130 mS/cm.

14. A purified dermonecrotic toxin of *Bordetella bronchiseptica* according to claim 11, wherein said toxin is prepared by the steps of:

(1) equilibrating a heparin-bound chromatographic gel by previously treating the chromatographic gel with a buffer having pH 7 to 9 and a specific electric conductivity ranging from 3 to 5 mS/cm, (2) bringing the dermonecrotic toxin-containing solution into contact with the heparin-bound chromatographic gel under conditions of pH 7 to 9, a temperature of 0 to 30° C., and a specific electric conductivity ranging from 3 to 5 mS/cm, (3) washing the heparin-bound chromatographic gel with a buffer having a pH of 5 to 10 and a specific electric conductivity ranging from 3 to 5 mS/cm prior to elution of dermonecrotic toxin from the chromatographic gel, and (4) eluting dermonecrotic toxin from the heparin-bound chromatographic gel by using a buffer having a pH of 5 to 10 and a specific electric conductivity ranging from 3 to 130 mS/cm.

* * * * *